(12) United States Patent
Steinbach

(10) Patent No.: US 8,808,231 B2
(45) Date of Patent: Aug. 19, 2014

(54) MULTIPLE RESERVOIR PROGRAMMABLE PUMP

(71) Applicant: Palyon Medical (BVI) Limited, Tortola (VG)

(72) Inventor: Bernd Steinbach, Friedberg (DE)

(73) Assignee: Palyon Medical (BVI) Limited (VG)

( * ) Notice: Subject to any disclaimer, the term of this patent is extended or adjusted under 35 U.S.C. 154(b) by 0 days.

(21) Appl. No.: 14/054,992

(22) Filed: Oct. 16, 2013

(65) Prior Publication Data
US 2014/0039384 A1   Feb. 6, 2014

Related U.S. Application Data

(63) Continuation of application No. 13/338,593, filed on Dec. 28, 2011, now Pat. No. 8,591,456.

(51) Int. Cl.
*A61M 31/00* (2006.01)

(52) U.S. Cl.
USPC .......................................................... 604/67

(58) Field of Classification Search
USPC .......................................................... 604/67
See application file for complete search history.

(56) References Cited

U.S. PATENT DOCUMENTS

| | | |
|---|---|---|
| 2,245,350 A | 6/1941 | Marshall |
| 3,951,147 A | 4/1976 | Tucker et al. |
| 4,003,379 A | 1/1977 | Ellinwood, Jr. |
| 4,193,397 A | 3/1980 | Tucker et al. |
| 4,258,711 A | 3/1981 | Tucker et al. |
| 4,544,371 A | 10/1985 | Dormandy, Jr. et al. |
| 4,548,607 A | 10/1985 | Harris |
| 4,588,394 A | 5/1986 | Schulte et al. |
| 4,634,427 A | 1/1987 | Hannula et al. |
| 4,668,231 A | 5/1987 | de Vries et al. |
| 4,699,615 A | 10/1987 | Fischell et al. |
| 4,714,462 A | 12/1987 | DiDomenico |
| 4,747,832 A | 5/1988 | Buffet et al. |
| 4,813,951 A | 3/1989 | Cannon |
| 4,828,551 A | 5/1989 | Gertler et al. |
| 4,838,887 A | 6/1989 | Idriss |
| 4,898,584 A | 2/1990 | Borsanyi et al. |
| 4,908,019 A | 3/1990 | Urquhart et al. |
| 4,969,873 A | 11/1990 | Steinbach et al. |
| 5,011,477 A | 4/1991 | Winchell et al. |
| 5,085,644 A | 2/1992 | Watson et al. |

(Continued)

FOREIGN PATENT DOCUMENTS

| | | |
|---|---|---|
| DE | 20311947 U1 | 11/2003 |
| EP | 1442760 A2 | 8/2004 |

(Continued)

OTHER PUBLICATIONS

Extended European Search Report for Application No. EP06771097 dated Feb. 14, 2013.

(Continued)

*Primary Examiner* — Jason Flick

(74) *Attorney, Agent, or Firm* — Lerner, David, Littenberg, Krumholz & Mentlik, LLP

(57) ABSTRACT

Different embodiment programmable pumps including multiple reservoirs are disclosed, as are methods of utilizing same. The pumps generally include at least two reservoirs and means for dispensing active substances housed in each at varying flow rates.

19 Claims, 30 Drawing Sheets

(56) References Cited

U.S. PATENT DOCUMENTS

| | | |
|---|---|---|
| 5,085,656 A | 2/1992 | Polaschegg |
| 5,146,933 A | 9/1992 | Boyd |
| 5,152,753 A | 10/1992 | Laguette et al. |
| 5,167,633 A | 12/1992 | Mann et al. |
| 5,176,644 A | 1/1993 | Srisathapat et al. |
| 5,205,820 A | 4/1993 | Kriesel |
| 5,207,666 A | 5/1993 | Idriss et al. |
| 5,236,689 A | 8/1993 | Wong et al. |
| 5,242,406 A | 9/1993 | Gross et al. |
| 5,304,153 A | 4/1994 | Tsujikawa |
| 5,336,194 A | 8/1994 | Polaschegg et al. |
| 5,667,504 A | 9/1997 | Baumann et al. |
| 5,716,343 A | 2/1998 | Kriesel et al. |
| 5,722,957 A | 3/1998 | Steinbach |
| 5,758,667 A | 6/1998 | Slettenmark et al. |
| 5,766,150 A | 6/1998 | Langkau |
| 5,769,823 A | 6/1998 | Otto et al. |
| 5,776,103 A | 7/1998 | Kriesel et al. |
| 5,785,688 A | 7/1998 | Joshi et al. |
| 5,792,104 A | 8/1998 | Speckman et al. |
| 5,814,019 A | 9/1998 | Steinbach et al. |
| 5,836,915 A | 11/1998 | Steinbach et al. |
| 5,840,063 A | 11/1998 | Flaherty |
| 5,895,428 A | 4/1999 | Berry |
| 5,906,597 A | 5/1999 | McPhee |
| 5,976,109 A | 11/1999 | Heruth |
| 6,086,555 A | 7/2000 | Eliasen et al. |
| 6,179,806 B1 | 1/2001 | Sansoucy |
| 6,280,416 B1 | 8/2001 | Van Antwerp et al. |
| 6,283,944 B1 | 9/2001 | McMullen et al. |
| 6,554,822 B1 | 4/2003 | Holschneider et al. |
| 6,620,151 B2 | 9/2003 | Blischak et al. |
| 6,652,510 B2 | 11/2003 | Lord et al. |
| 6,673,091 B1 | 1/2004 | Shaffer et al. |
| 6,730,060 B1 | 5/2004 | Steinbach et al. |
| 6,764,472 B1 | 7/2004 | Burke et al. |
| 6,796,956 B2 | 9/2004 | Hartlaub et al. |
| 6,805,693 B2 | 10/2004 | Gray et al. |
| 6,902,544 B2 | 6/2005 | Ludin et al. |
| 6,932,114 B2 | 8/2005 | Sparks |
| 7,044,932 B2 | 5/2006 | Borchard et al. |
| 7,083,593 B2 | 8/2006 | Stultz |
| 7,108,686 B2 | 9/2006 | Burke et al. |
| 7,150,741 B2 | 12/2006 | Erickson et al. |
| 7,214,221 B2 | 5/2007 | Fentress et al. |
| 7,367,968 B2 | 5/2008 | Rosenberg et al. |
| 7,708,730 B2 | 5/2010 | Steinbach et al. |
| 8,002,747 B2 * | 8/2011 | Lord et al. .................... 604/131 |
| 2002/0151875 A1 | 10/2002 | Haller |
| 2002/0156361 A1 | 10/2002 | Popowski et al. |
| 2002/0156462 A1 | 10/2002 | Stultz |
| 2003/0175149 A1 | 9/2003 | Searles et al. |
| 2003/0199813 A1 | 10/2003 | Struble |
| 2004/0078000 A1 | 4/2004 | Borchard et al. |
| 2004/0143242 A1 | 7/2004 | Ludin et al. |
| 2005/0070875 A1 * | 3/2005 | Kulessa ........................ 604/500 |
| 2005/0113745 A1 | 5/2005 | Stultz |
| 2005/0273082 A1 | 12/2005 | Olsen |
| 2005/0277912 A1 | 12/2005 | John |
| 2006/0089619 A1 | 4/2006 | Ginggen |
| 2006/0253105 A1 * | 11/2006 | Ludin et al. ................ 604/891.1 |
| 2006/0271021 A1 | 11/2006 | Steinbach |
| 2006/0271022 A1 * | 11/2006 | Steinbach et al. ......... 604/891.1 |
| 2007/0185470 A1 | 8/2007 | Steinbach et al. |
| 2009/0227989 A1 | 9/2009 | Burke et al. |
| 2009/0281494 A1 | 11/2009 | Das |

FOREIGN PATENT DOCUMENTS

| | | |
|---|---|---|
| JP | 02046867 A | 2/1990 |
| JP | 02174860 A | 7/1990 |
| JP | 2001178816 A | 7/2001 |
| WO | 0066204 A1 | 11/2000 |
| WO | 03022338 A1 | 3/2003 |
| WO | 03/068049 | 8/2003 |
| WO | 2005007223 | 1/2005 |
| WO | 2005044343 | 5/2005 |
| WO | 2005079885 | 9/2005 |
| WO | 2006127841 A2 | 11/2006 |
| WO | 2006127923 A2 | 11/2006 |

OTHER PUBLICATIONS

Institute for Safe Medication practices, "Template for disaster? Fatal Injection into Wrong Port of Implanted Infusion Pump", Jan. 15, 2004.

International Search Report and Written Opinion for Application No. PCT/EP2012/068102 dated Dec. 19, 2012.

International Search Report, PCT/US06/20135 dated Feb. 14, 2007.

International Search Report, PCT/US07/01828 dated Sep. 23, 2008.

Karas, Beverly Schambura, "Refilling an implanatable pump", Nov. 1995.

Medtronic Educational Brief, "Pump Refill Techniques"ISOMED Pump Systems, Aug. 2003.

Supplementary Partial European Search Report, EP 07716956, mailed Aug. 8, 2009.

Udelsman et al., "Intraperitoneal delivery of insulin via mechanical pump:surgical implications", Mar. 3, 2000, Langenbeck's Arch Surg (2000) 385:367-372.

* cited by examiner

MULTIPLE RESERVOIR PROGRAMMABLE PUMP

CROSS-REFERENCE TO RELATED APPLICATIONS

The present application is a continuation of U.S. patent application Ser. No. 13/338,593, filed on Dec. 28, 2011, the disclosure of which is hereby incorporated by reference herein.

BACKGROUND OF THE INVENTION

The present invention relates to a multiple reservoir implantable pump that is programmable so as to allow for varying flow rates of active substances from each of the reservoirs to be delivered to a patient.

Implantable pumps have been well known and widely utilized for many years. Typically, pumps of this type are implanted into patients who require the delivery of medication or other fluids (hereinafter referred to as "active substances") to specific areas of their body. For example, patients that are experiencing severe pain may require pain killers daily or multiple times per day. Absent the use of an implantable pump or the like, a patient of this type would be subjected to one or more painful injections of such active substances. In the case of pain associated with more remote areas of the body, such as the spine, these injections may be extremely difficult to administer and particularly painful for the patient. Furthermore, attempting to treat conditions such as this through oral or intravascular administration of an active substance often requires higher doses and may cause severe side effects. Therefore, it is widely recognized that utilizing an implantable pump may be beneficial to both a patient and the treating physician.

Many implantable pump designs have been proposed. For example, U.S. Pat. No. 4,969,873 ("the '873 patent"), the disclosure of which is hereby incorporated by reference herein, teaches one such design. The '873 patent is an example of a constant flow pump, which typically includes a housing having two chambers, a first chamber for holding the active substance to be administered to the patient, and a second chamber for holding a propellant. A flexible membrane separates the two chambers such that expansion of the propellant in the second chamber pushes the active substance out of the first chamber. This type of pump also typically includes an outlet opening connected to the first chamber on one end and a catheter or other delivery device for directing the active substance to the desired area of the body on the other, a replenishment opening for allowing refilling of the first chamber, and a bolus opening for allowing the direct introduction of an active substance through the catheter without introduction into the first chamber. Both the replenishment and bolus openings are covered by septa that allow a needle or similar device to be passed therethrough, but which seal the openings upon removal of the needle. As pumps of this type provide a constant flow of active substance to the specific area of the body, they must be refilled periodically with a proper concentration of active substance suited for extended release.

Implantable pumps may also be of the programmable type, meaning that they can provide variable flow rates of an active substance therefrom. While these types of programmable pumps have typically involved the use of a solenoid pump or peristaltic pump, certain pumps similar to the above-discussed constant flow pumps have been modified in order to provide the ability of providing varying flow rates of an active substance from the pump. For instance, U.S. Patent Application Publication Nos. 2007/0005044 and 2007/0112328, the disclosures of which are hereby incorporated by reference herein, teach such pumps. However, those pumps are limited to a single active substance chamber.

Implantable pumps having multiple reservoirs are also known in the art. For instance, U.S. Patent Application Publication No. 2006/0271022 ("the '022 Publication"), the disclosure of which is hereby incorporated by reference herein, teaches a multiple reservoir pump design. While that reference also teaches such a multiple reservoir implantable pump that employs a patient controlled actuation mechanism, as well as a method of varying flow rate from the pump by modifying the amounts of active substance included in each of its multiple reservoirs (to allow multiple fixed flow rates), it does not teach a programmable type pump. The benefits of such a programmable pump are widely known from the previous incarnations that included a single active substance chamber. However, heretofore, there have not been any suitable incarnations of such a pump.

Therefore, there exists a need for a programmable multiple reservoir implantable pump.

BRIEF SUMMARY OF THE INVENTION

A first aspect of the present invention is a programmable pump system for dispensing first and second active substances at varying flow rates to a patient. In accordance with one embodiment of this first aspect, the pump system includes a pump housing defining an interior including a first chamber containing the first active substance, a second chamber containing the second active substance, and a third chamber containing a propellant; a first valve in fluid communication with the first chamber; a second valve in fluid communication with the second chamber; and a catheter fluidly connected with the first and second chambers. Preferably, expansion of the propellant within the third chamber causes the first active substance to flow from the first chamber at a first flow rate towards the catheter and the second active substance to flow from the second chamber at a second flow rate towards the catheter, actuation of the first valve varies the first flow rate, and actuation of the second valve varies the second flow rate.

Other embodiments of the first aspect may include a pump where the first and second active substances are identical. The pump may further include first and second membranes defining the third chamber. The housing may include first and second portions, the first and second membranes captured between the first and second portions so that the first portion and first membrane defines the first chamber and the second portion and second membrane defines the second chamber. First and second pressure sensors may be associated with the first chamber and third and fourth pressure sensors associated with the second chamber, wherein a comparison of pressure readings taken by the first and second pressure sensors determines whether the first valve should be actuated and a comparison of pressure readings taken by the third and fourth pressure sensors determines whether the second valve should be actuated.

In still other embodiment, the pump may further include a first motor for actuating the first valve and a second motor for actuating the second valve. The actuation of the first and second valves may occurs in planes parallel to planes of the top and bottom of the pump housing or in perpendicular planes thereof. The pump may further include a first offset cam associated with the first motor and first valve and a second offset cam associated with the second motor and second valve, where rotation of the first offset cam by the first motor causes the first valve to actuate and rotation of the second offset cam by the second motor causes the second valve to actuate. A first lever may be associated with the first motor and first valve and a second lever may be associated with the second motor and second valve, where movement of the first lever by the first motor causes the first valve to actuate and movement of the second lever by the second motor causes the second valve to actuate.

The pump may be configured such that the first and second pressure sensors and first motor are contained within a first hermetic housing and the third and fourth pressure sensors and second motor are contained within a second hermetic housing. Those hermetic housings may be constructed of titanium, and welded together so as to be sealed from fluid and/or gas. The first hermetic housing may include a first aperture covered by a first membrane and the second hermetic housing includes a second aperture covered by a second membrane. The first membrane may be associated with the first motor and the first lever and the second membrane may be associated with the second motor and the second lever.

The pump may also include a third hermetic housing associated with the first and second hermetic housings. The third hermetic housing may include at least one power source and at least one electronic component, such as a processing unit. The pump may include a replenishment opening for use in filling the first chamber with the first active substance and the second chamber with the second active substance. The pump may further include a third valve in fluid communication with the replenishment opening and first and second chambers. When the third valve is in a first position only the first chamber can be refilled and when the third valve is in a second position only the second chamber can be refilled. The pump may include an actuation mechanism for actuating the third valve between the first and second positions.

BRIEF DESCRIPTION OF THE DRAWINGS

A more complete appreciation of the subject matter of the present invention and the various advantages thereof, can be realized by reference to the following detailed description in which reference is made to the accompanying drawings in which.

DETAILED DESCRIPTION

In describing the preferred embodiments of the subject matter illustrated and to be described with respect to the drawings, specific terminology will be used for the sake of clarity. However, the invention is not intended to be limited to any specific terms used herein, and it is to be understood that each specific term includes all technical equivalents which operate in a similar manner to accomplish a similar purpose.

Figure 1:
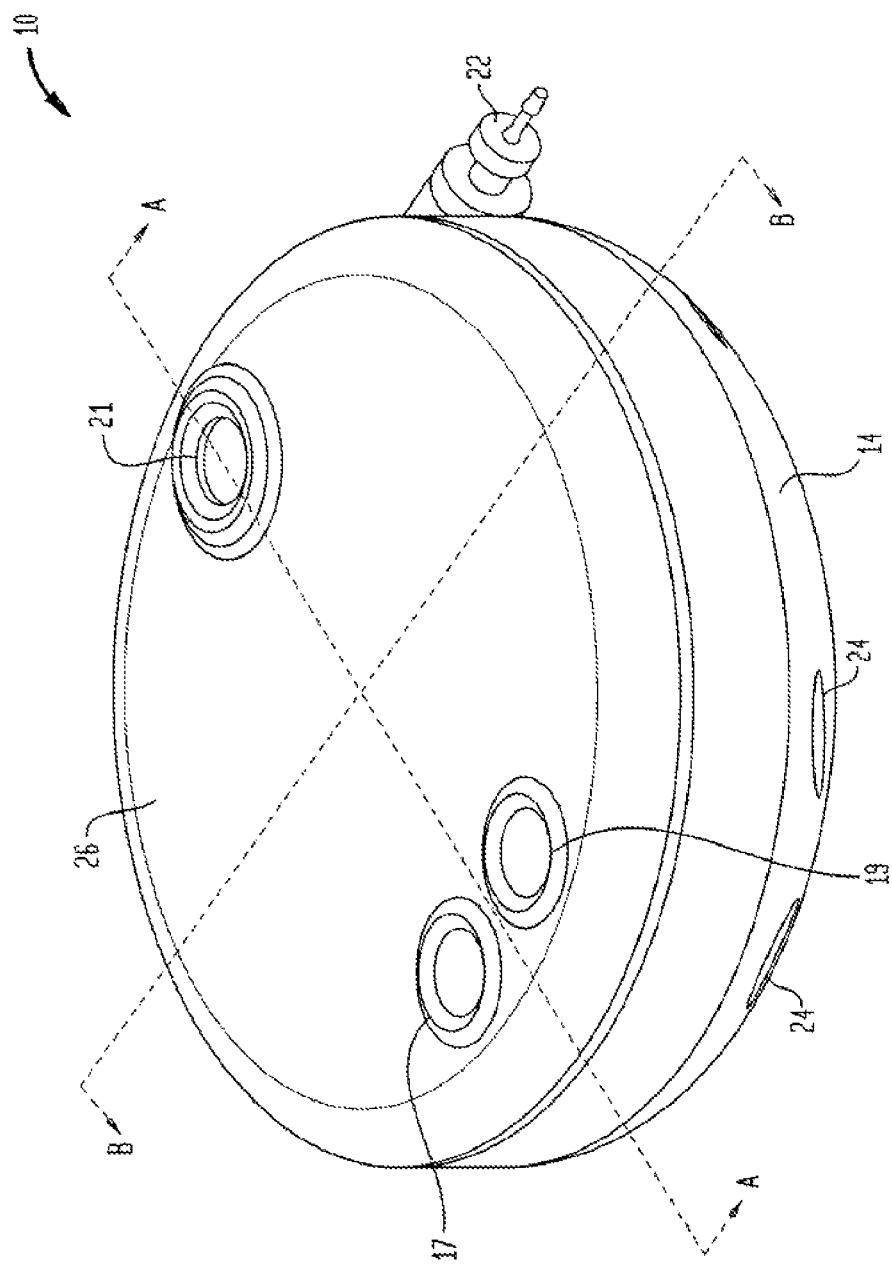
FIG. 1 is a top perspective view of a multiple reservoir implantable pump in accordance with an embodiment of the present invention.
Figure 2:
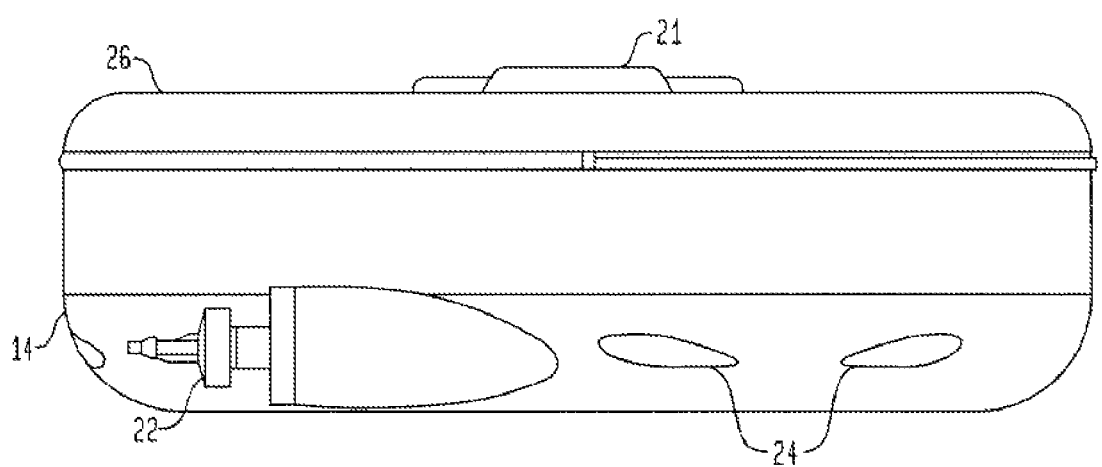
FIG. 2 is a side view of the implantable pump shown in FIG. 1.

Referring to the drawings wherein like referenced numerals refer to like elements, there is shown in FIG. 1, in accordance with an embodiment of the present invention, a multiple reservoir implantable pump designated generally by reference number 10. Pump 10 includes upper portion 12 (best shown in FIGS. 3-6, 8, and 9) and lower portion 14, which are mechanically attached to one another. This attachment is discussed further below, but it is to be understood that while certain exemplary attachments are discussed, others may be employed in pump 10. Upper portion 12 includes three apertures 16, 18, and 20 (best shown in FIGS. 8 and 9) formed therein that partially define a lower reservoir port, an upper reservoir port, and catheter direct access port, respectively. As will be discussed more fully below, the upper and lower reservoir ports are for use in refilling the upper and lower reservoirs of the pump, while the catheter direct access port is for use in a direct injection of an active substance into the catheter (thusly bypassing other components of the pump). Lower portion 14 includes a catheter connector 22 extending therefrom (best shown in FIG. 2) as well as several sutures holes 24 suitable for receiving a suture for fixing pump 10 to a portion of the body (once again best shown in FIG. 2). Upper portion 12 also has a cap 26 attached thereto that includes apertures 17, 19, and 21 corresponding to apertures 16, 18, and 20, respectively, to partially define the lower reservoir port, upper reservoir port, and catheter direct access port noted above.

Figure 3:
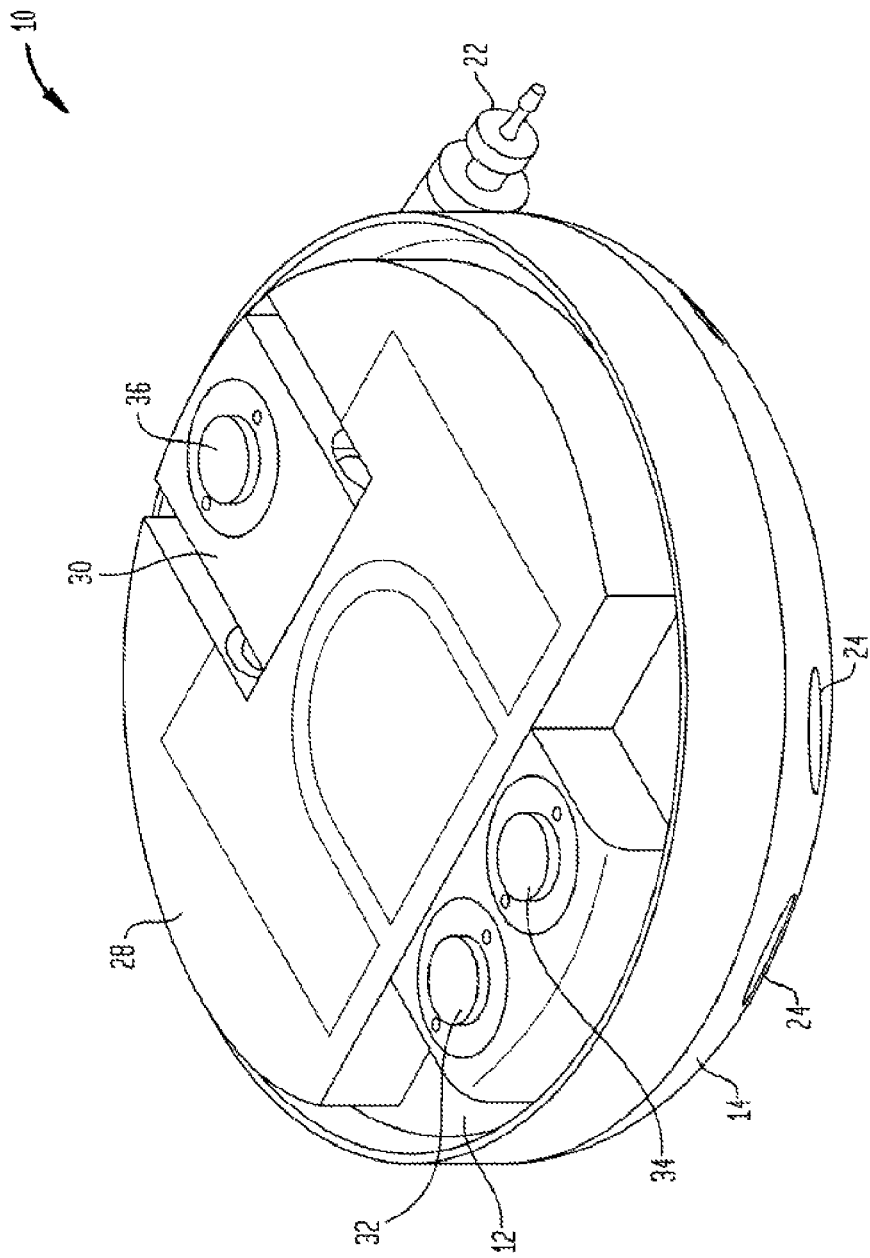
FIG. 3 is a top perspective view of the implantable pump shown in FIG. 1 with a cap removed.

FIG. 3 depicts pump 10 having cover 26 removed therefrom so that it can be seen that upper portion 12 further includes hermetic titanium housing 28 and a valve housing 30. Further, although they are shown in other of the figures, FIG. 3 highlights a first septum 32 associated with the lower reservoir port, a second septum 34 associated with the upper reservoir port, and a third septum 36 associated with the catheter direct access port. Such septa may be of any well known construction in the art and may be formed of any suitable material, such as silicone rubber. Preferably, the septa allow for insertion of a needle therethrough during a refill or direct injection operation, and closure after removal of the needle therefrom. Septa 32 is preferably fit within aperture 16 (with aperture 17 overlying it), septa 34 is preferably fit within aperture 18 (with aperture 19 overlying it), and septa 36 is preferably fit within aperture 20 (with aperture 21 overlying it).

Figure 4:
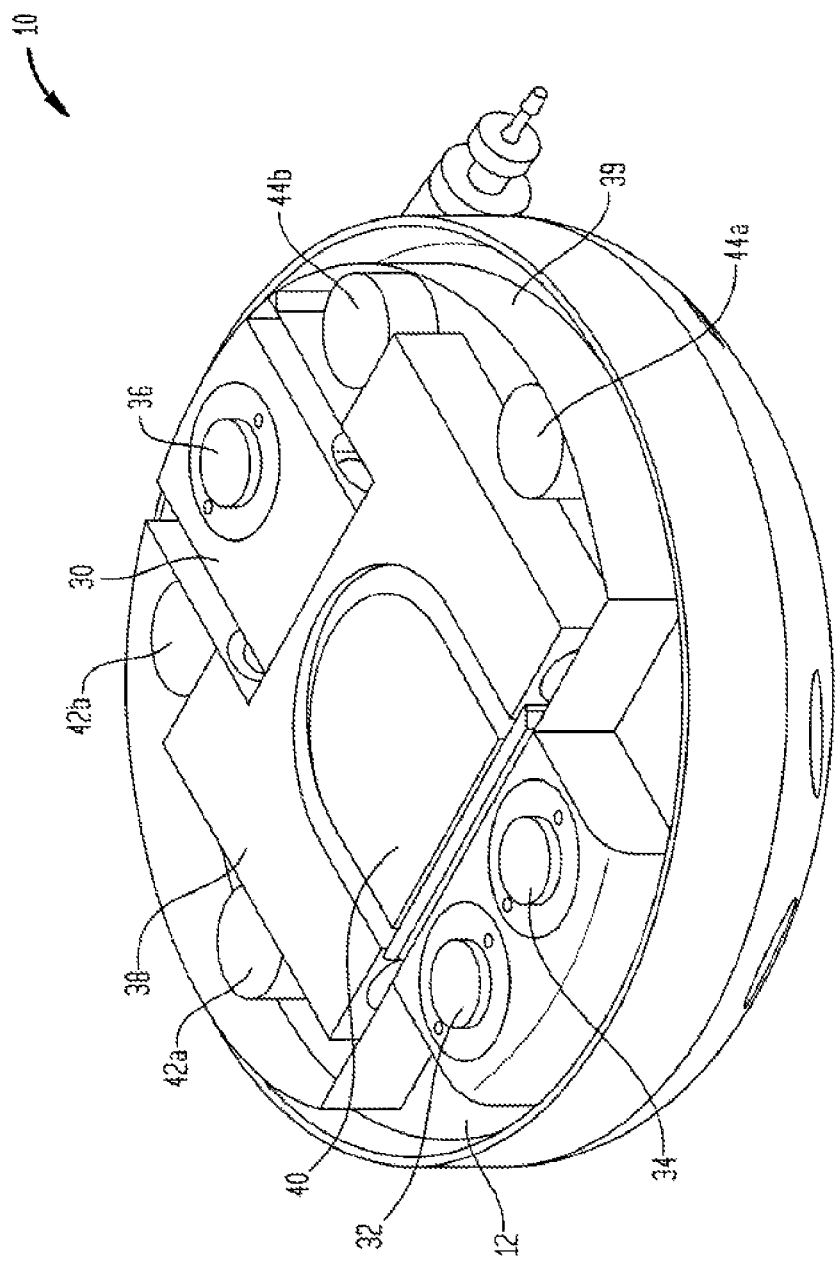
FIG. 4 is a top perspective view similar to the one shown in FIG. 3, with a housing cover removed therefrom.

FIG. 4 depicts pump 10 having a top portion or housing cover of hermetic housing 28 removed therefrom. As can be seen in that drawing, housing 28 further includes a component support 38, a wall 39 surrounding and enclosing housing 28, a battery 40, a first set of pressure sensors 42*a* and 42*b*, and a second set of pressure sensors 44*a* and 44*b*. All of these components will be discussed more fully below in the discussion pertaining to the operation of pump 10. In a preferred embodiment, housing 28 includes outer portions formed of titanium. These portions, including the aforementioned top portion or housing cover are welded together so as to hermetically retain the other noted components within the housing. This is important, as several of the components are susceptible to damage if exposed to fluids within the body of a patient in which pump 10 is implanted. For instance, battery 40 and portions of pressure sensors 42*a*, 42*b*, 44*a*, and 44*b* are prone to damage if exposed to bodily fluids.

Figure 5:
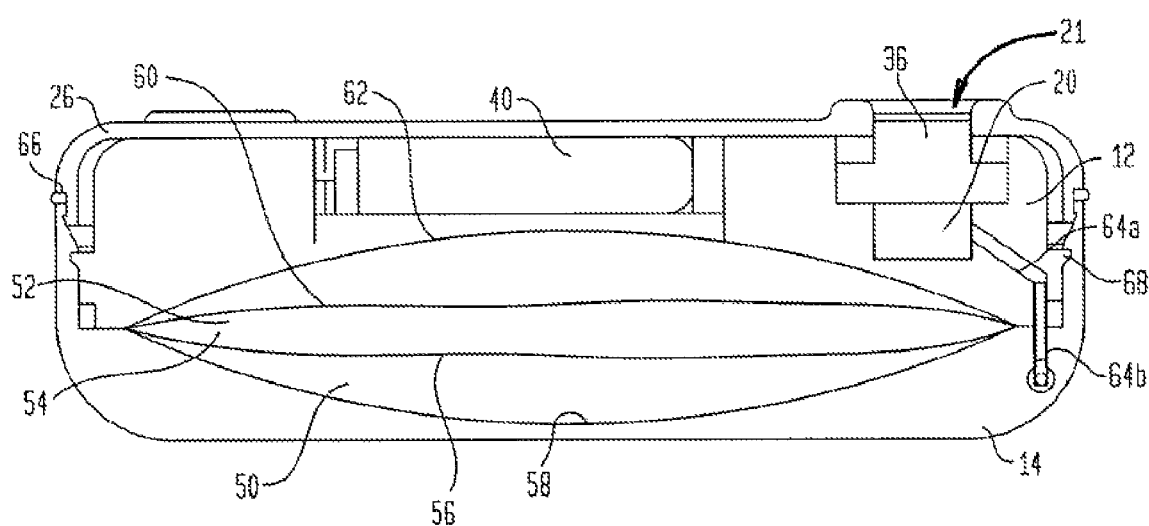
FIG. 5 is a cross-sectional view of the implantable pump shown in FIG. 1 taken along line A-A.

FIG. 5 is a cross-sectional view of pump 10 taken along the line A-A of FIG. 1, where it is shown that the pump also includes a lower reservoir 50, an upper reservoir 52, and a propellant chamber 54 flanked therebetween. Specifically, lower reservoir 50 is formed between a first flexible membrane 56 and a concave portion 58 of lower portion 14, while upper reservoir 52 is formed between a second flexible membrane 60 and a concave portion 62 of upper portion 12. Propellant chamber 54 is formed between and by flexible membranes 56 and 60. This is not unlike the design taught in the above-discussed '022 Publication. It is to be understood that while portions 58 and 60 are shown as being concave, any other shape is contemplated, including but not limited to, undulating shapes or the like. Moreover, FIG. 5 depicts apertures 20 and 21 and septum 36 of the catheter direct access port, as well as passages 64*a* and 64*b* which fluidly connect port 20 to the catheter. Thus, any active substance injected into the catheter direct access port will go directly through the catheter without passing through any of the other components of the pump. FIG. 5 also depicts a snap-fit connection 66 between cover 26 and upper portion 12, and a similar snap-fit connection 68 between upper portion 12 and lower portion 14. While snap-fit connections are indeed shown in the embodiment depicted in the figures, other connections are contemplated, including screwable connections and/or more permanent connections such as the use of adhesives, or the like. In addition, although shown as being constructed of a polymer material (e.g., PEEK), upper portion 12, lower portion 14, and cover 26 (as well as other components of pump 10) may be constructed out of metallic materials, such as stainless steel or titanium. In such a case, the different components may be connected together in different manners, such as through the use of welds or the like.

Figure 6:
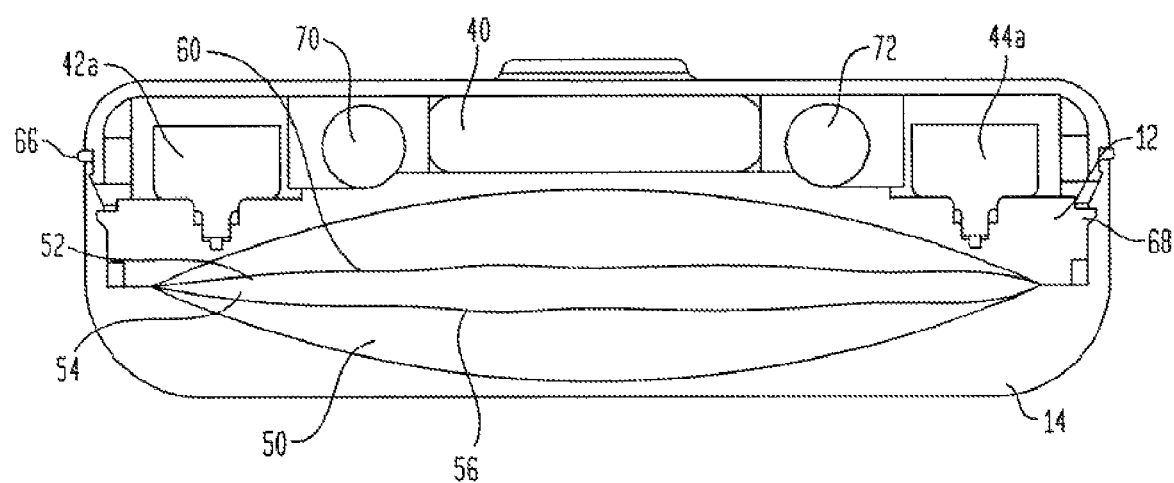
FIG. 6 is a cross-sectional view of the implantable pump shown in FIG. 1 taken along line B-B.

FIG. 6 is a cross-sectional view taken along line B-B of FIG. 1. Once again, lower reservoir 50, upper reservoir 52, and propellant chamber 54 can be seen in this drawing, as can flexible membranes 56 and 60. Sensors 42*a* and 44*a* are also shown in FIG. 6. Essentially, sensor 42*a* senses the pressure of an active substance being contained in lower reservoir 50, while sensor 44*a* senses the pressure of fluid being contained in upper reservoir 52. The fluid directed to these sensors may be directed as part of the dispensing operation or could be separately provided via a duct not associated with the dispensing operation. The pressure values obtained by such sensors are electronically captured by an electrical unit included in hermetic housing 28 (discussed more fully below) and utilized in varying the flow rates of active substance from pump 10. FIG. 6 also depicts a portion of micromotors 70 and 72, both of which will be discussed more fully below.

Figure 7:
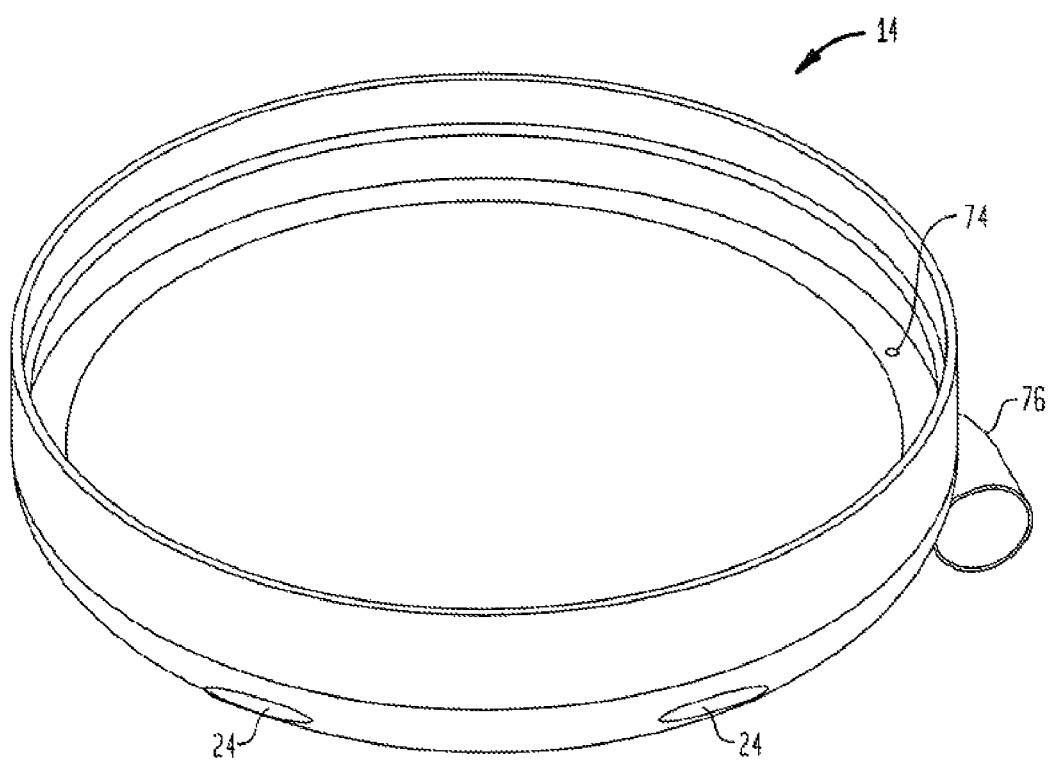
FIG. 7 is a top perspective view of a lower portion of the implantable pump shown in FIG. 1.

Lower portion 14 is shown in FIG. 7 separated from upper portion 12. As can be seen in that figure, a duct 74 is formed in the bottom of portion 14 in order to allow fluid to flow from passage 64*b* to the catheter. Moreover, FIG. 7 depicts an interface 76 for reception of catheter connector 22. Interface 76 is essentially a cylindrical formation designed to partially house connector 22. Of course, many different configurations may be employed for both interface 76 and catheter connector 22. Likewise, it is contemplated for connector 22 or the like to be formed integral with lower portion 14 or any other portion of pump 10.

Figure 8:
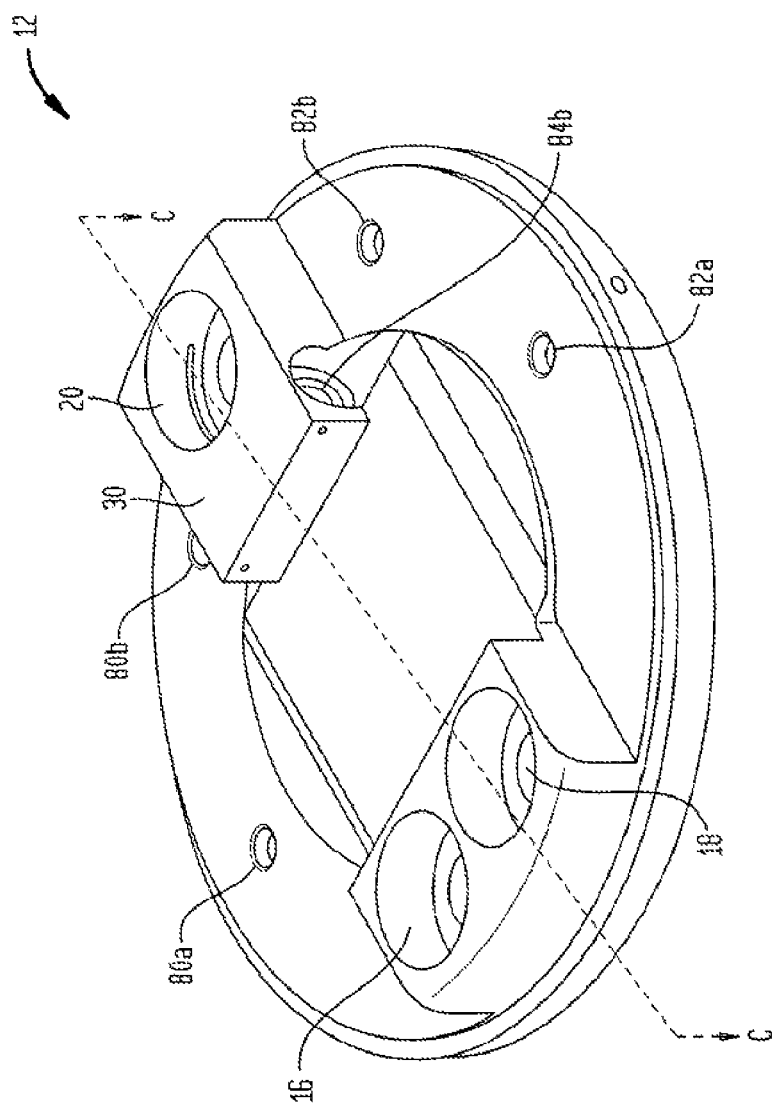
FIG. 8 is a top perspective view of an upper portion of the implantable pump shown in FIG. 1, with certain components removed therefrom.
Figure 9:
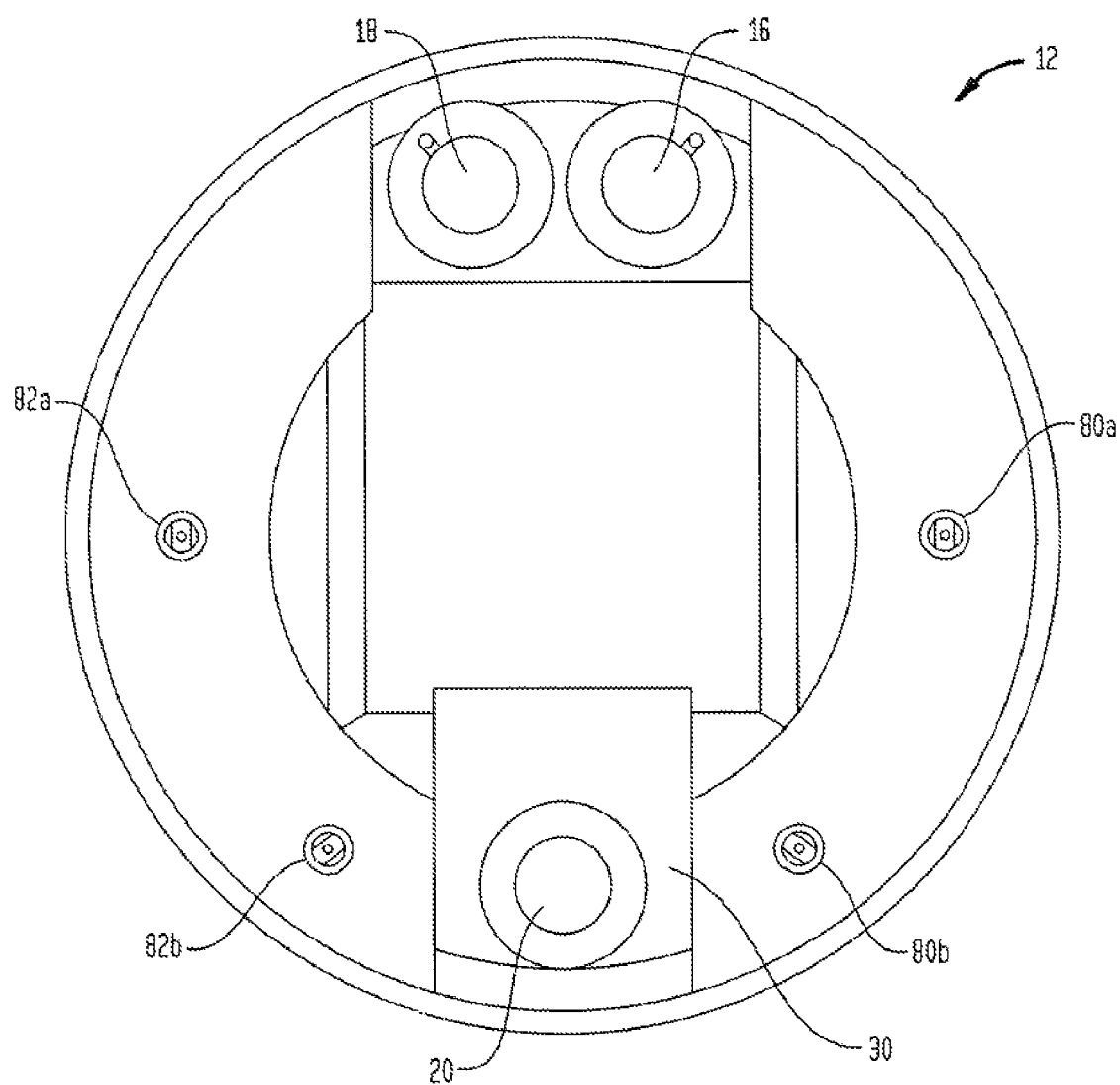
FIG. 9 is a top view of the upper portion shown in FIG. 8.

FIGS. 8 and 9 depict upper portion 12 having all other components removed therefrom, including, cover 26, hermetic housing 28, septa 32, 34, and 36, component support 38, battery 40, and sensors 42*a*, 42*b*, 44*a*, and 44*b*. Apertures 16, 18, 20, can clearly be seen, as can the entirety of valve body 30. Also shown are sensor ports 80*a* and 80*b* for reception of sensors 42*a* and 42*b*, and sensor ports 82*a* and 82*b* for reception of and fluid communication with sensors 44*a* and 44*b* are shown. These ports are essentially apertures that both hold the sensors in place and allow fluid to be directed thereto. With specific reference to FIG. 9, each of ports 80*a*, 80*b*, 82*a*, and 82*b* are shown as including an opening that allows for the active substance from different portions of pump 10 to be delivered to the sensors. Valve body 30 is also shown in FIG. 8 as including a valve aperture 84*b*, with a like valve aperture 84*a* on an opposite side of the valve body (not shown in FIG. 8).

Figure 10:
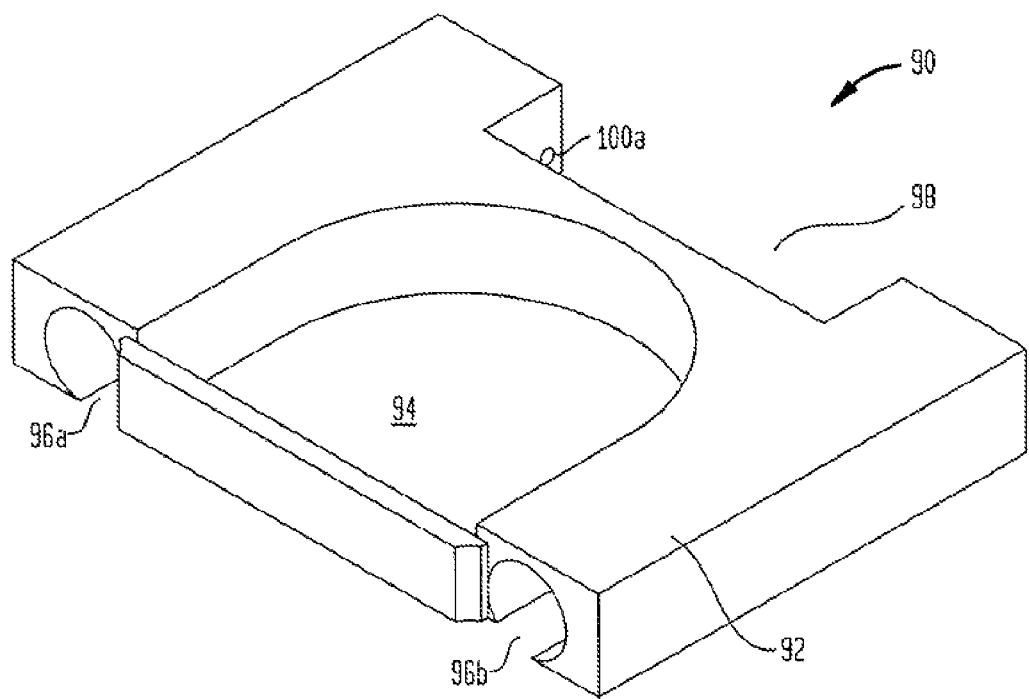
FIG. 10 is a perspective view of a component support removed from the implantable pump shown in FIG. 1.

Component support 38 is shown apart from the remainder of pump 10 in FIG. 10. The support includes a main body 92 that defines a battery compartment 94 for receiving battery 40, motor apertures 96*a* and 96*b* for receiving motors 70 and 72, respectively, slot 98 for receiving a portion of valve body 30, and guiding cylinders 100*a* and 100*b* (the latter of which is not shown in FIG. 10) for receiving push rods associated with the two valves included in implantable pump 10. With reference back to FIG. 4, it can be seen that component support 90 is received within a central portion of upper portion 12, so that slot 98 receives a portion of valve body 30 therein. Battery 40 is also shown disposed in battery compartment 94 in FIG. 4.

Figure 11:
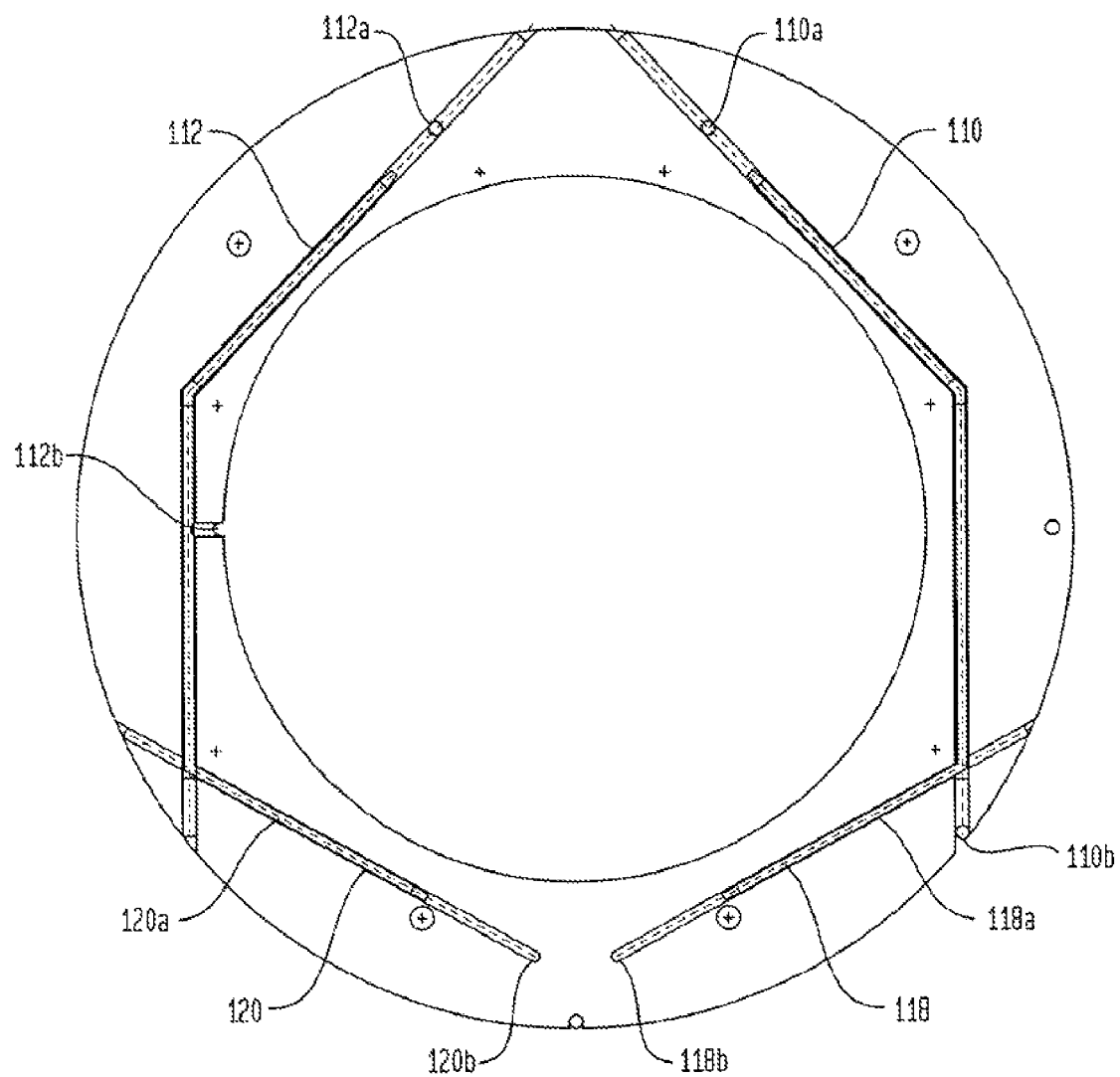
FIG. 11 is a cross-sectional view of the upper portion shown in FIG. 8 taken along line C-C.
Figure 12:
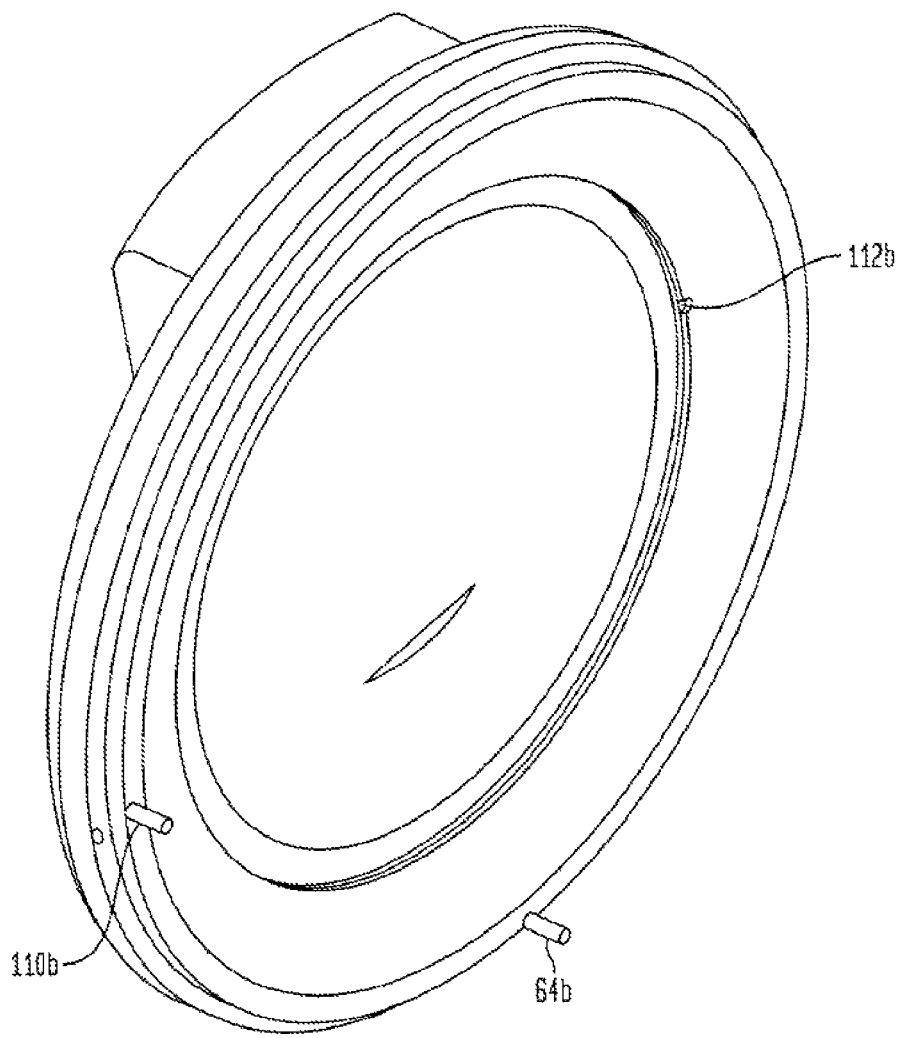
FIG. 12 is a bottom perspective view of the upper portion shown in FIG. 8.

Some of the various ducts included in upper portion 12 can be seen in the cross-sectional view of FIG. 11, which is taken through line C-C of FIG. 8. The ducts are generally formed by drilling through portions of upper portion 12 and inserting glass tubes or the like. This manufacturing process may also include the closure of certain ends of the drilled channels after insertion of the tubing, for instance, through the use of core pins or the like. These ducts allow for fluid to flow from upper and lower reservoirs 50 and 52, to the above-mentioned pressure sensors and valves, as well as from the upper and lower reservoir refill ports and the catheter direct access port ultimately to the catheter (not shown). Specifically, fluid injected into the lower reservoir port enters duct 110 through a first opening 110a and exits via a second opening/duct portion 110b where it is ultimately led to lower reservoir 50. Likewise, fluid injected into the upper reservoir port enters duct 112 through a first opening 112a and exits via a second opening 112b where it is led to upper reservoir 52. As noted above, passages 64a and 64b facilitate fluid injected into the catheter direct access port to flow directly to the catheter (as shown in FIG. 5). FIG. 12 demonstrates where passage 64b, second opening/duct portion 110b and second opening 112b are situated. Moreover, an opening is provided in duct 110 and is in communication with port 80a (shown schematically in FIG. 15) and opening 112a is in communication with both upper reservoir 52 and portion 82a. Thus, the pressure of active substance flowing from lower reservoir 50 and upper reservoir 52 may be measured by sensors 42a and 44a, respectively.

A duct 118 is also provided and connected with duct 110. Duct 118 is preferably a capillary having a filter along at least a portion thereof. Duct 118 includes a first opening 118a which is in fluid communication with portion 82b and sensor 42b, and a second portion 118b that is in fluid communication with a first valve. Similarly, a duct 120 is also provided as a capillary having a filter along at least a portion thereof. Duct 120 is connected with duct 112 and includes a first opening 120a that is in fluid communication with portion 80a and sensor 44b, and a second portion 120b that is in fluid communication with a second valve. This allows for active substance to be directed from each of the reservoirs to the respective valves (discussed below), where the active substance flow can be varied. Specifically, fluid dispelled from lower reservoir 50 passes through opening 110b to opening 114 where a first pressure reading can be taken by sensor 42a. Fluid dispelled from lower reservoir 50 also travels through duct 118, where it is put into contact with sensor 42b and ultimately passes to the first valve via second portion 118b. Likewise, fluid dispelled from upper reservoir 52 passes through opening 112b where a first pressure reading can be taken by sensor 44a. Fluid dispelled from upper reservoir 52 also passes through duct 112 and into duct 120, where it is put into contact with sensor 44b and ultimately passes to the second valve via second portion 118b. The sensors preferably take measurements directly from each reservoir (sensors 42a and 44a) and just prior to entering a portion of ducts 118 and 120 that allow for a maximum flow of the fluid (sensors 42b and 44b). These readings can be utilized to determine the flow rate of the fluid.

Figure 13:
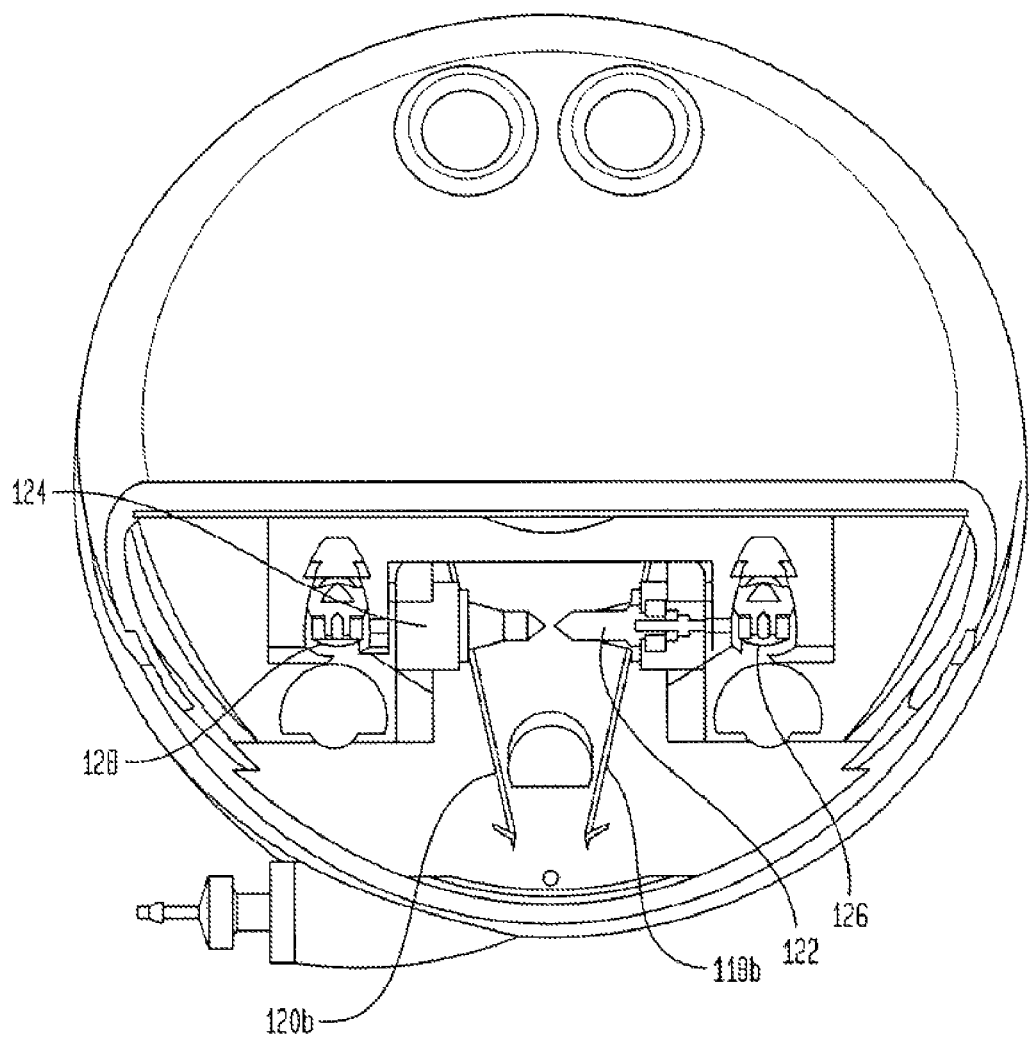
FIG. 13 is a partial cross-sectional top view of the implantable pump shown in FIG. 1.
Figure 14:
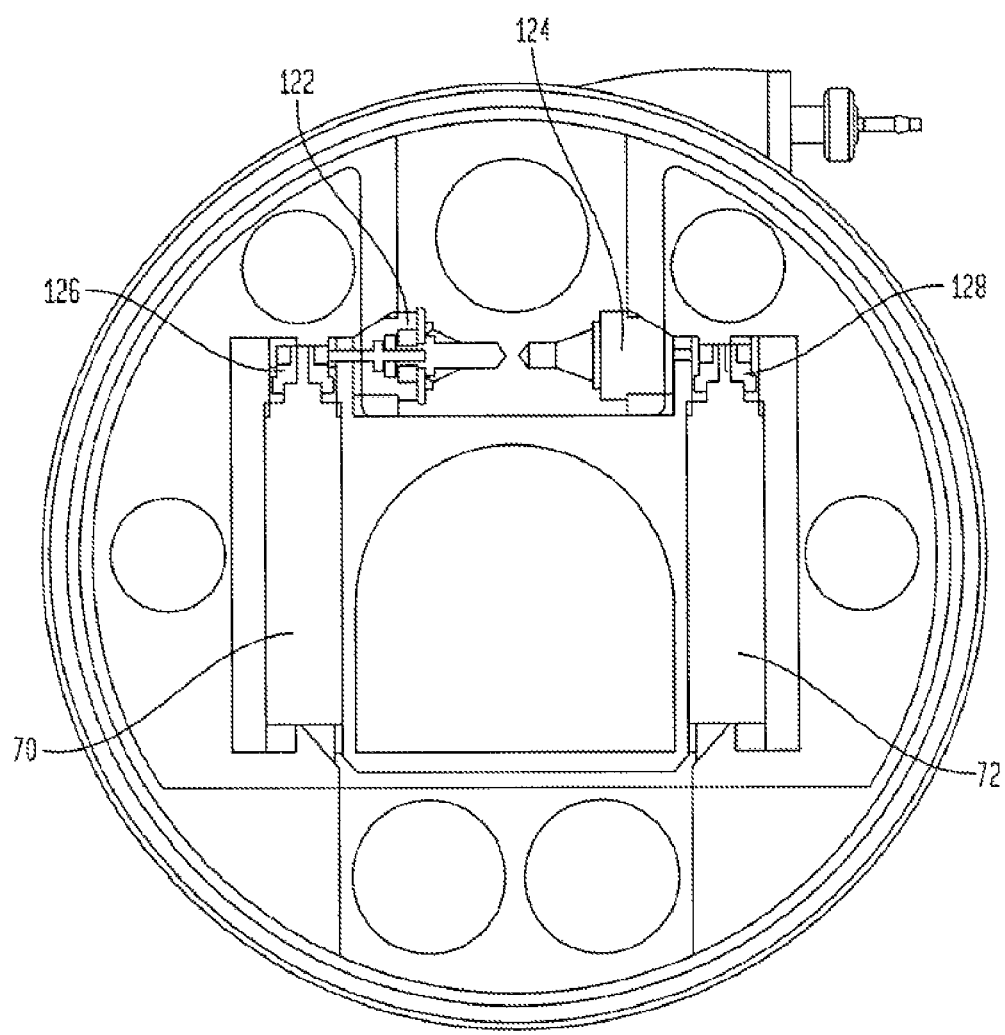
FIG. 14 is a cross-sectional top view of the implantable pump shown in FIG. 1.

FIGS. 13 and 14 depict valves 122 and 124 and their relationship to the other components of pump 10. Specifically, fluid flows to valve 122 from lower reservoir 50 by second portion 118b and fluid flows to valve 124 from upper reservoir 52 by second portion 120b, as is discussed above. Active substance dispelled by each of those reservoirs is introduced into the valves, which can be actuated to allow for varying of flow rate from them. Specifically, motor 70 is utilized to rotate an offset cam 126 to actuate valve 122, while motor 72 is utilized to rotate an offset cam 128 to actuate valve 124. The tapering shape of the valves means that this actuation can result in more or less blockage of the flow path of the active substance, thereby allowing for more or less flow rate from the pump.

Propellant chamber 54 preferably includes a propellant that expands under normal body temperature, such as those known in the prior art and discussed in the '022 Publication. For instance, in one embodiment, propellant chamber 54 is filled with hexafluorobutane. When pump 10 is implanted, the propellant expands thereby causing a displacement of membranes 56 and 60, which, in turn, causes an active substance contained within reservoirs 50 and 52 to be dispelled therefrom. As discussed above, an active substance housed within lower reservoir 50 flows to both sensors 42a and 42b, while an active substance housed within upper reservoir flows to both sensors 44a and 44b. The pressure readings taken by the sensors 42a and 42b and 44a and 44b are compared by a processing unit located in pump 10 (not shown) in order to calculate the flow rate based upon the pressure differential. At this point, the electrical unit can also determine if one or both of the valves should be further actuated in order to arrive at the desired flow rate from pump 10 of each active substance. This desired flow rate can be input via an external programmer as is know in the art, or could be controlled by the electrical unit itself.

Figure 15:
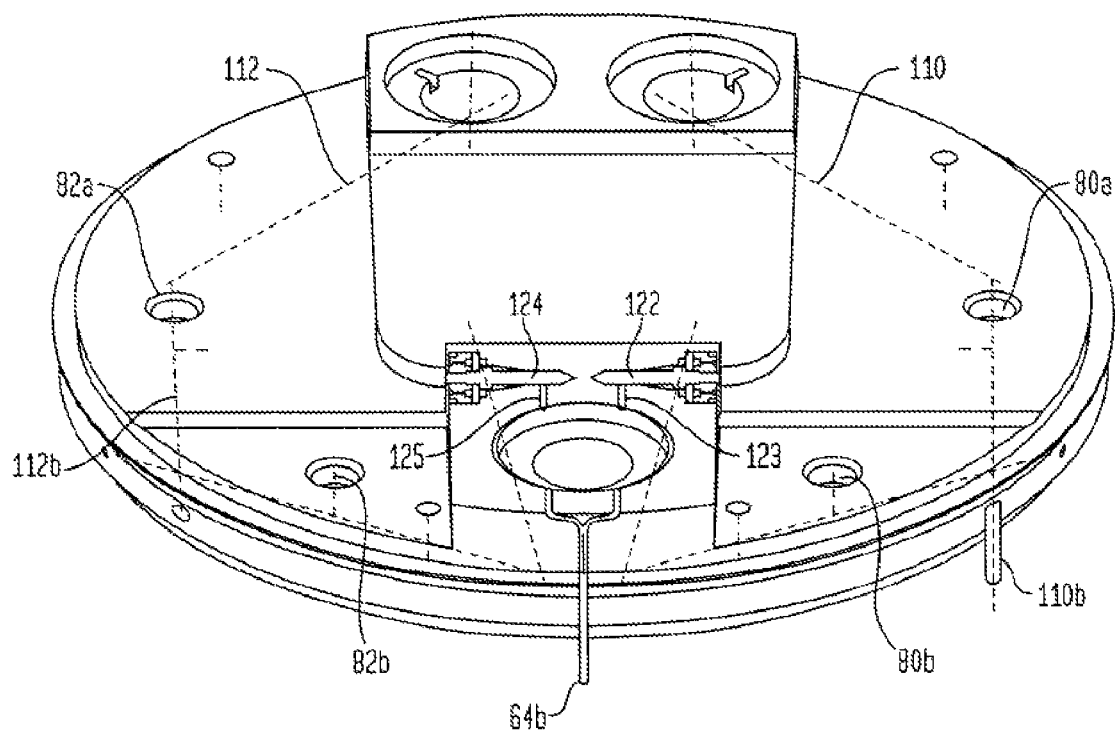
FIG. 15 is a partial transparent view of the upper portion shown in FIG. 8.

FIG. 15 depicts the path by which fluid that has passed by valves 122 and 124 takes. Specifically, fluid that passes by valve 122 proceeds through a duct 123 and fluid that passes by valve 124 proceeds through a duct 125. Each of these ducts extend around the catheter direct access port and feed into a collector manifold, not unlike that shown in FIG. 28. This manifold essentially collects fluid directly injected into the catheter direct access port (via passage 64a) and fluid from valves 122 and 124 so that such can ultimately be passed to the catheter through passage 64b.

Figure 16:
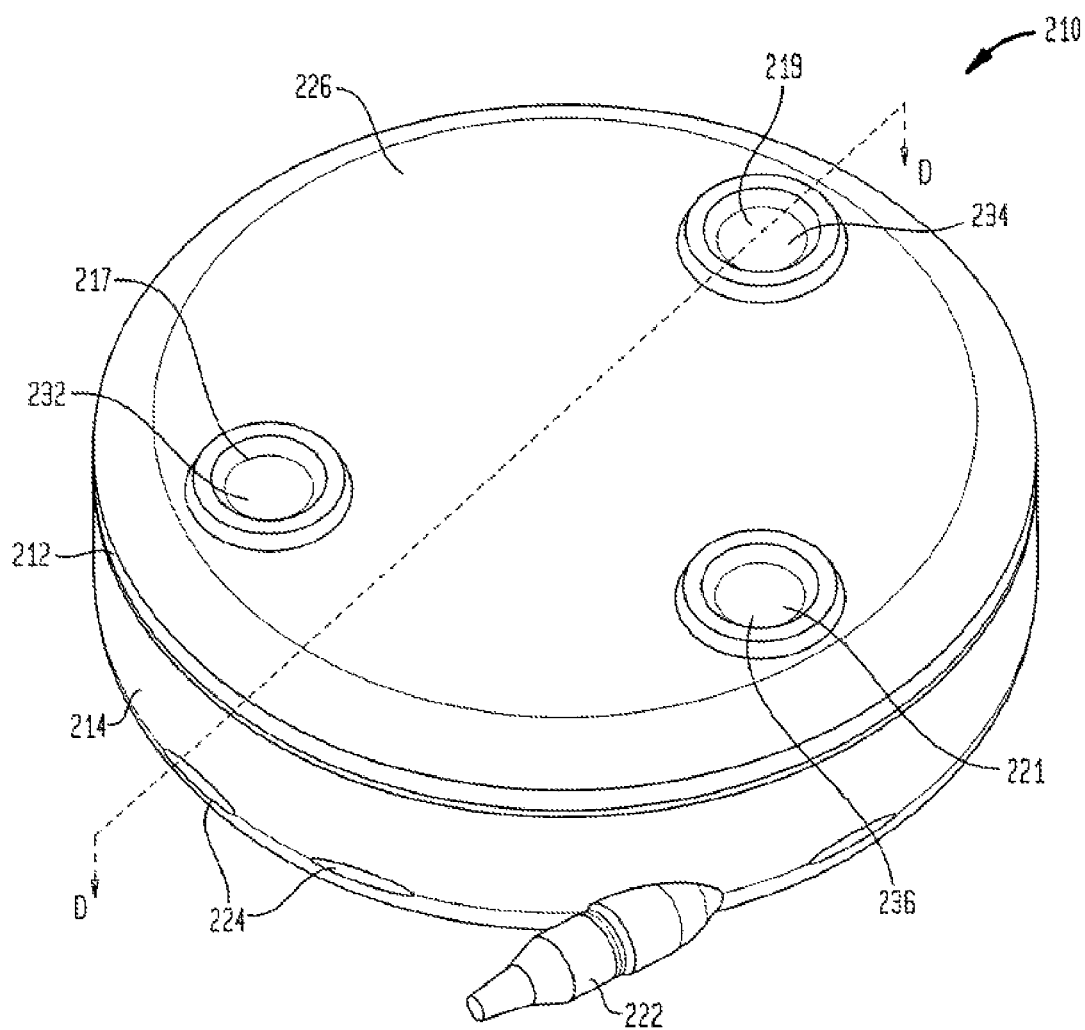
FIG. 16 is a top perspective view of a multiple reservoir implantable pump in accordance with another embodiment of the present invention.

FIG. 16 depicts a second embodiment pump 210. Where possible, like reference numerals for like elements to that of pump 10 are utilized, with such numbers being set forth in the 200-series of numbers. Pump 210 operates in a similar manner to pump 10, albeit with some different structure being employed. Like pump 10, pump 210 includes upper portion 212 and lower portion 214, which are mechanically attached to one another. This attachment may be similar to attachment of like elements discussed above in connection with pump 10, but also may be any other suitable attachment mechanism.

Figure 17:
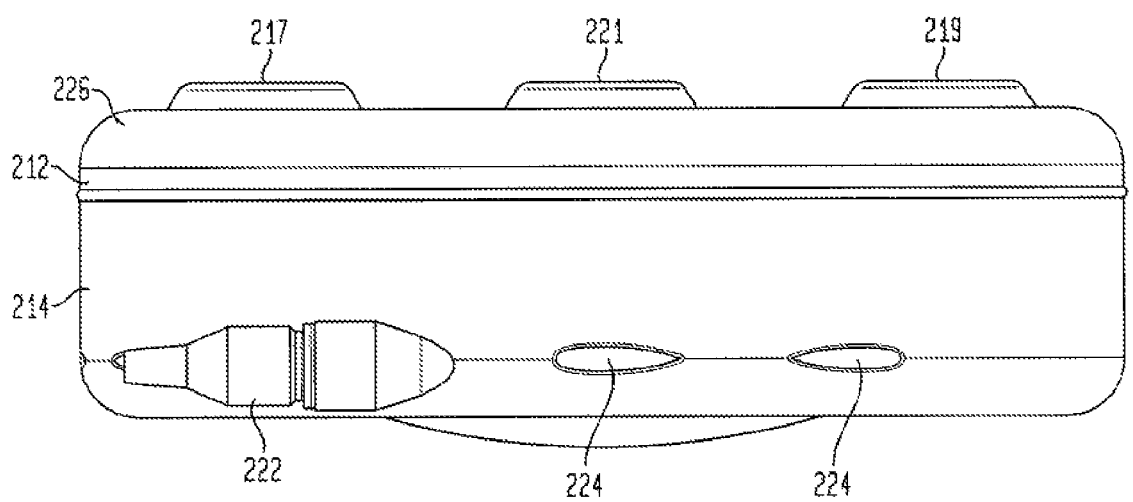
FIG. 17 is a side view of the implantable pump shown in FIG. 16.

Upper portion 212 includes three apertures formed therein that partially define a lower reservoir port, an upper reservoir port, and catheter direct access port, respectively. These ports also include septa 232, 234, and 236, respectively. Like in pump 10, lower portion 214 also includes a catheter connector 222 extending therefrom (best shown in FIG. 17) as well as several sutures holes 224 suitable for receiving a suture for fixing pump 210 to a portion of the body (once again best shown in FIG. 17). Upper portion 212 also has a cap 226 attached thereto that includes apertures 217, 219, and 221 corresponding to the apertures of upper portion 212, respectively, to partially define the lower reservoir port, upper reservoir port, and catheter direct access port noted above.

Figure 18:
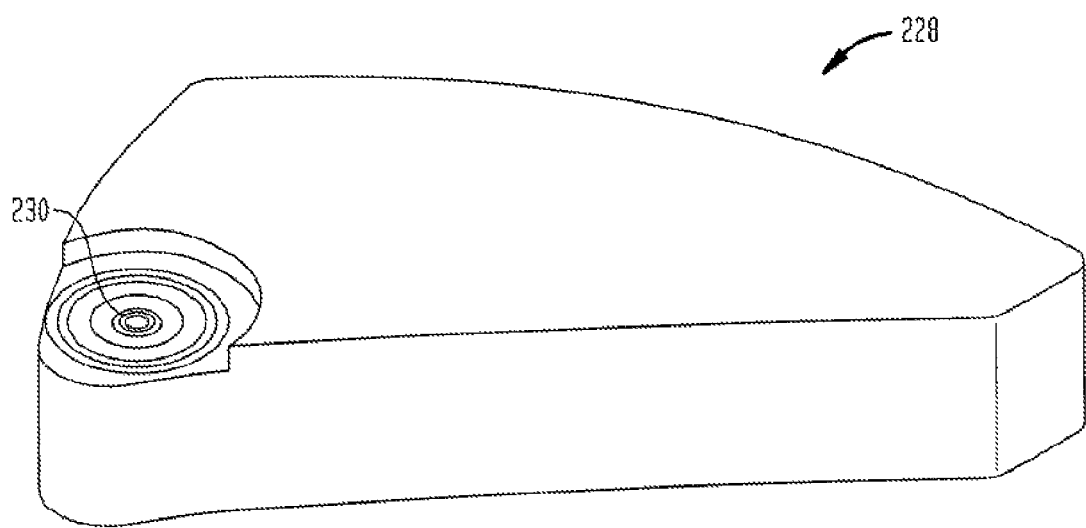
FIG. 18 is a top perspective view of a portion of a hermetic housing included in the implantable pump shown in FIG. 16.
Figure 19:
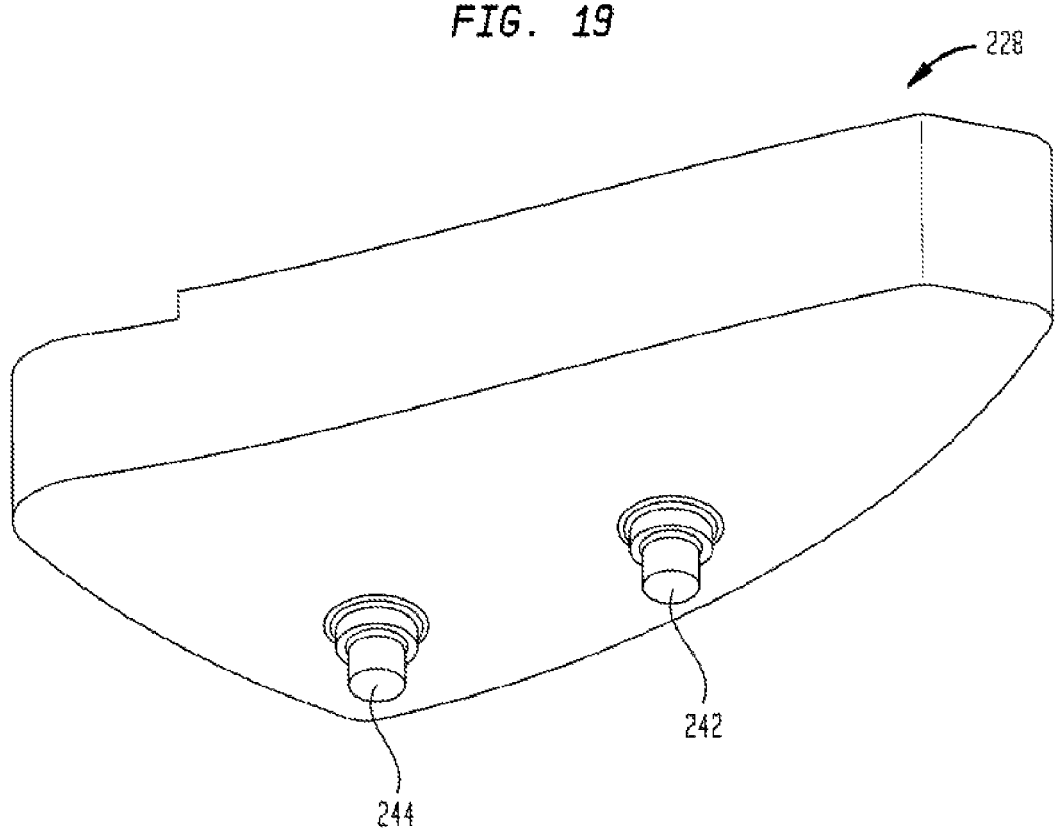
FIG. 19 is a bottom perspective view of the hermetic housing shown in FIG. 18.
Figure 20:
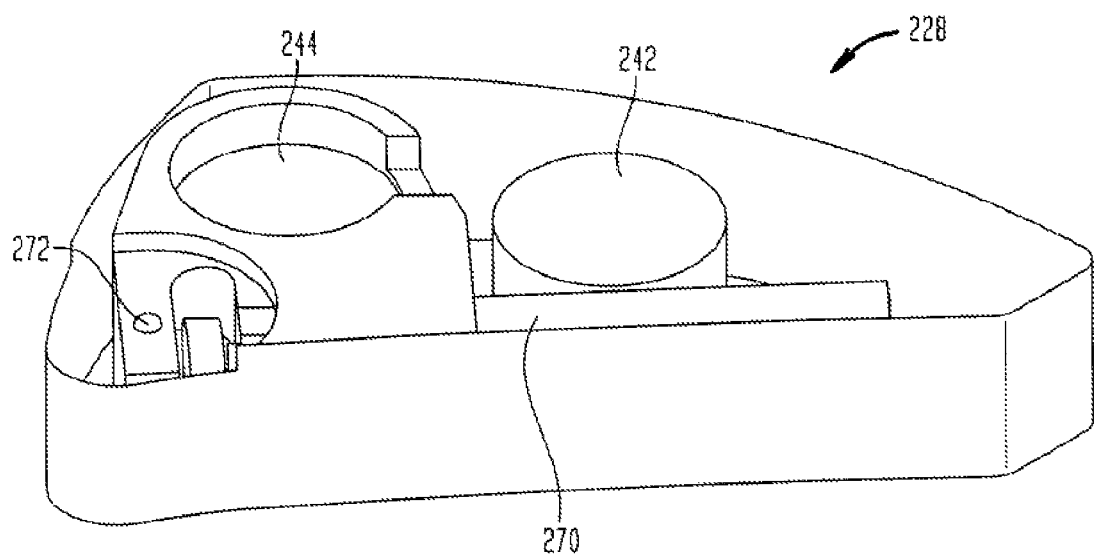
FIG. 20 is a top perspective view of the hermetic housing shown in FIG. 18, with a cover portion removed

FIGS. 18-20 depict one portion of a three part hermetic housing included in pump 210. Specifically, those figures depict one of two housings 228 that in addition to housing 229 (discussed below) make up the hermetic housing. Housing 228 is similar to housing 28 of pump 10, but is designed so as to house the components useful in varying the flow rate of an active substance dispensed from one of the upper and lower reservoirs included in pump 210. Moreover, housings 228 do not include valves or electronic components. The former are disposed in a portion of upper portion 212, while the latter are formed in a separate hermetic housing 229 (best shown in FIG. 21). This will all be discussed further below. Each housing 228 is preferably made of titanium or other suitable material and includes a membrane 230 formed on an exterior surface thereof, which essentially overlies an aperture formed through the housing.

As is best shown in FIG. 20, disposed on the interior of the housing is a set of pressure sensors 242 and 244, a motor 270, and a valve actuation pin 272. Pin 272 is preferably moved via an eccentric (not shown) connected with motor 270. Pressure sensor 242 is designed to measure the pressure of fluid being dispelled from one of the upper and lower reservoirs, while sensor 244 is designed to measure the pressure of fluid after it has been passed through a resistor capillary and before passing through a valve (discussed below). FIG. 19 depicts a portion of sensors 242 and 244 extending below housing 228, so as to allow for the fluid to come into contact with the sensors.

Figure 21:
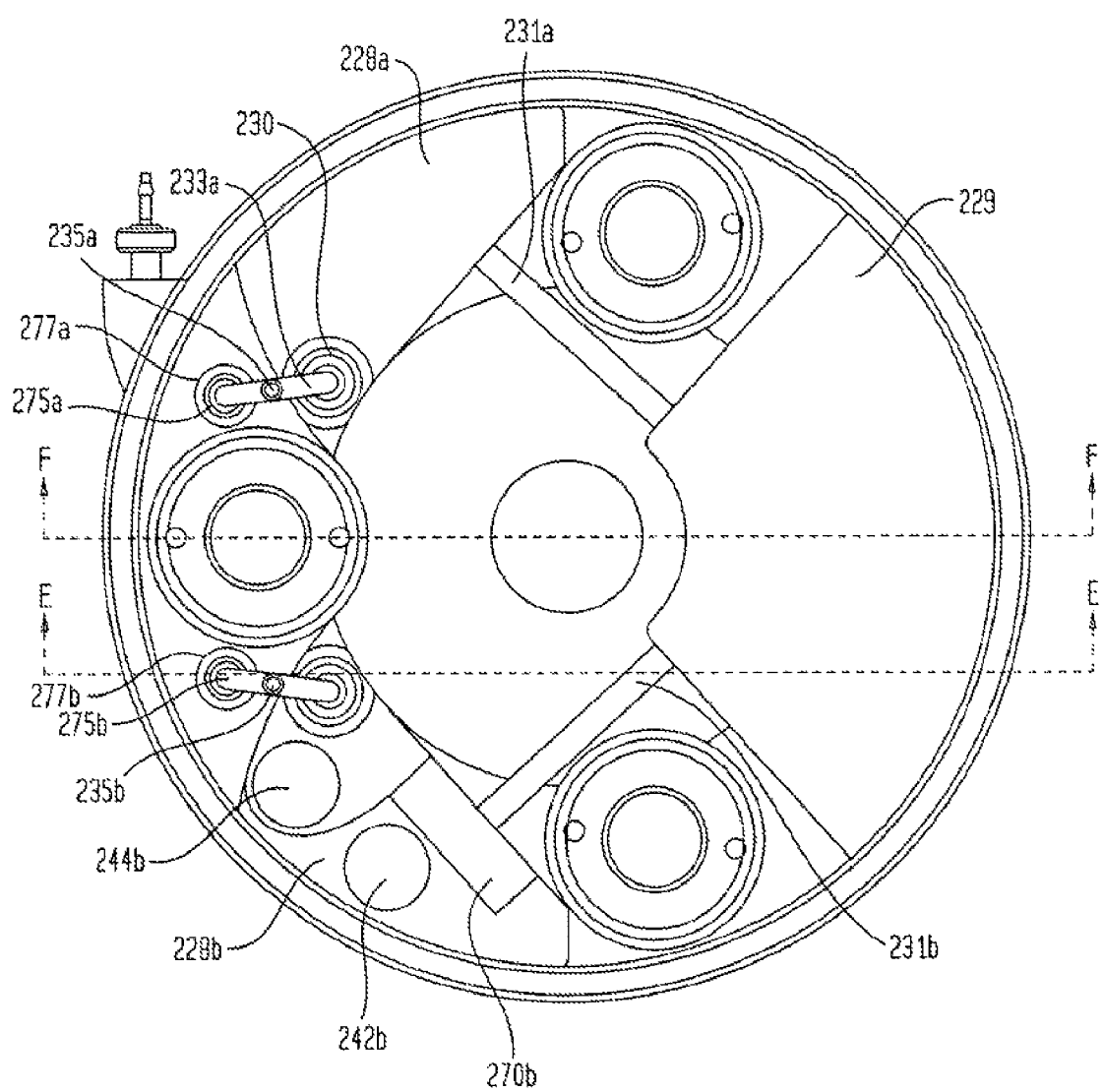
FIG. 21 is a top cross sectional view of the implantable pump shown in FIG. 16 taken along line D-D of FIG. 16.

FIG. 21 depicts a cross-sectional top view of pump 210, which illustrates several additional components of the pump, plus the orientation of housings 228 and housing 229. For the purposes of the below discussion, the housing associated with the lower reservoir will be labeled and referred to as housing 228a, while the housing associated with the upper reservoir will be labeled and referred to as housing 228b. Components of each housing will also be referred to with the 'a' and 'b' identifier. As is shown, housings 228a, 228b (shown with a top portion thereof removed), and 229 are situated on three different sides of pump 210. Connecting duct 231a connects housing 228a with housing 229 and connecting duct 231b connects housing 228b with housing 229, so that the electrical components housed within housing 229 can communicate with the sensors and motor disposed in each housing 228a and 228b.

FIG. 21 also depicts an actuation lever 233a which is engaged with membrane 230a on one side and with a valve 275a on the other and an actuation lever 233b which is engaged with membrane 230b on one side and with valve 275b on the other. These levers are preferably pivotable about a center point, much like a "see saw." More particularly, lever 233a is pivotable about a center point which includes an adjustment screw 235a and lever 233b is pivotable about a center point which includes an adjustment screw 235b. These adjustment screws allow for the relationship between the valves and levers to be adjusted, which in turn allows for the fine tuning of the fluid dispelling operation. During operation, valve 275b, which is preferably biased to an open position, is moved by lever 233b. Specifically, operation of motor 270b rotates the eccentric (not shown), which in turn moves pin 272. The pin in turn moves membrane 230b, which in turn moves lever 233b to either apply or release a force upon valve 275b. In the preferred embodiment shown, valve 275b is biased via an elastic element 277b. Of course, the particular arrangements depicted are only one fashion in which the housings can be configured, and other configurations may be employed.

Figure 22:
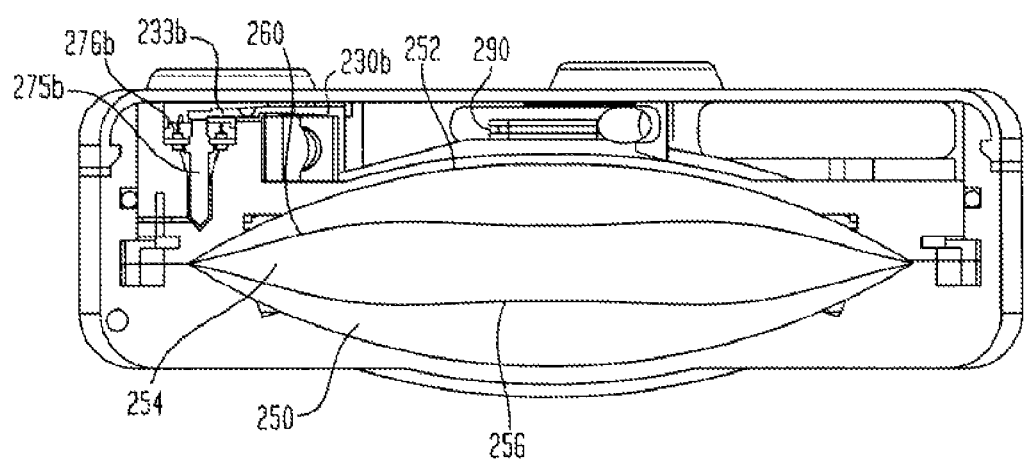
FIG. 22 is a cross sectional view of the implantable pump shown in FIG. 17 taken along line E-E of FIG. 21.

FIG. 22 is a cross-sectional view of pump 210 taken along the line E-E of FIG. 21, where it can be seen that pump 210 includes a lower reservoir 250 and an upper reservoir 252, and a propellant chamber 254 defined by membranes 256 and 260. This not unlike that of pump 10, and like that embodiment, variations in the design shown are contemplated. FIG. 21 also depicts the design and orientation of valve 275b which is shown as being of a similar design to the valves included in above-discussed pump 10. However, valve 275b (as well as valve 275a) is situated in a vertical orientation, as opposed to the horizontal orientation depicted in pump 10. The structure and orientation of lever 233b can also be seen in FIG. 22. Reference is made here to the above discussion pertaining to the operation of lever 233b, and it is noted that lever 233b may be spring actuated or the like so that it itself can bias valve 275b in an opposite direction (i.e., downwards in the view shown in FIG. 22) absent the force provided by membrane 230b, pin 272b, and motor 270b. It is to be understood that while only one set of components is discussed (i.e., those in and associated with housing 228b), the same structure and orientation applies to the other (i.e., those in and associated with housing 228a).

FIG. 22 also depicts an antenna assembly 290, which is shown in that figure outside of the hermetic house, but preferably is located within housing 229. The antenna assembly preferably includes a mounting 292 around which a wire or series of wires (not show) are wound. This structure is electrically coupled with other components of housing 229, so as to allow for wireless remote connection with such components. If the antenna is to be located outside of hermetic housing 229, the coupling could be via a feed-through (not shown). It is to be noted that a ferrite core could be utilized to reduce the overall size of the antenna.

Figure 23:
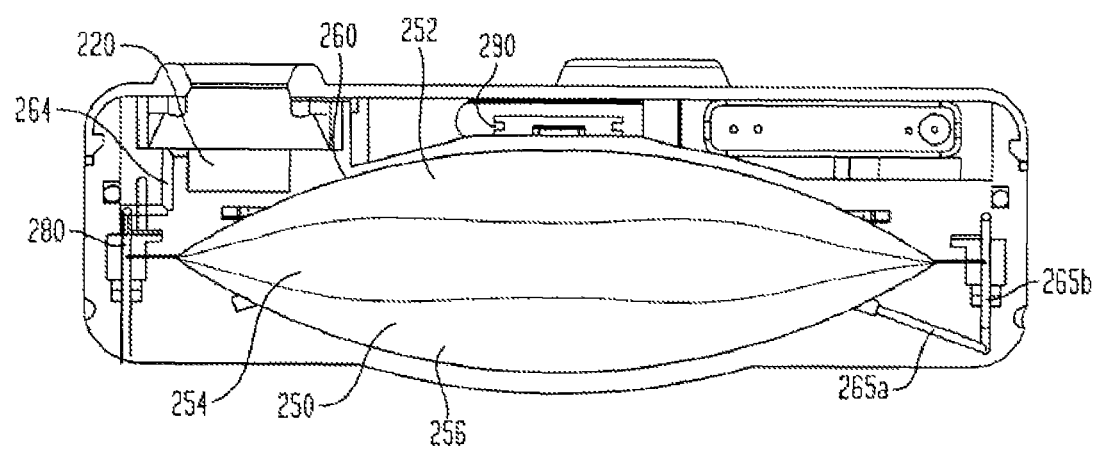
FIG. 23 is a cross sectional view of the implantable pump shown in FIG. 15 taken along line F-F of FIG. 21.
Figure 24:
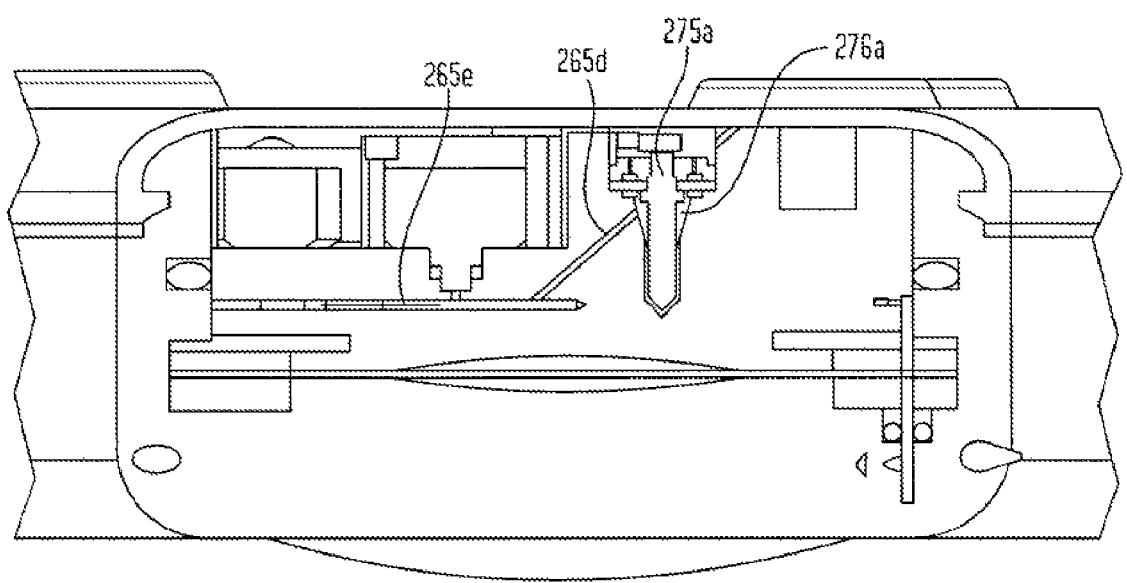
FIG. 24 is a cross sectional view of the implantable pump shown in FIG. 16 taken along line G-G of FIG. 21.
Figure 28:
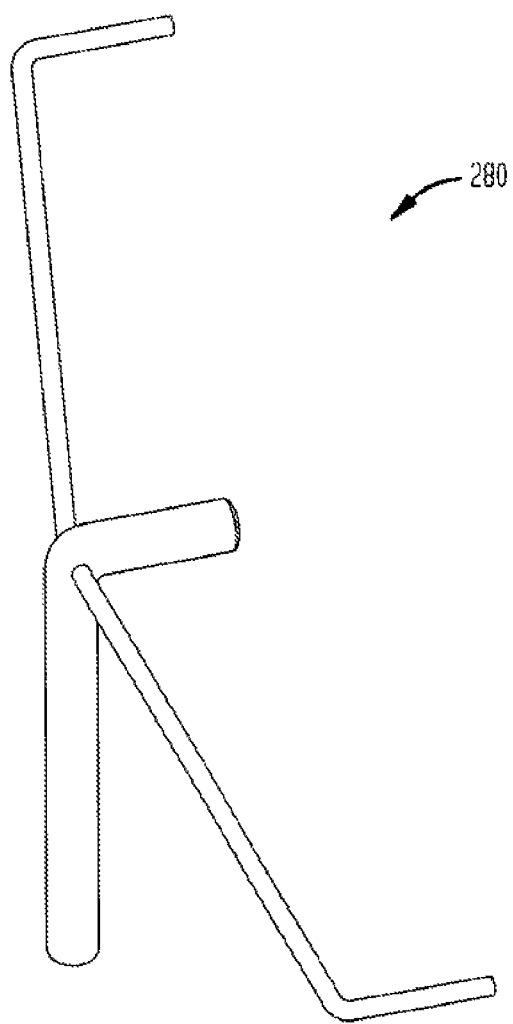
FIG. 28 is a perspective view of a collector manifold.

FIG. 23 is another cross-sectional view of pump 210 taken along the line F-F of FIG. 21, where lower reservoir 250, upper reservoir 252, and propellant chamber 254 can once again be seen. Moreover, FIG. 23 depicts catheter direct access port 220 and a duct network 264 that directs fluid injected through port 220 directly to a collector manifold 280, as is shown in FIG. 28 and discussed further below. Manifold 280, in turn, directs directly injected fluid to catheter connector 222, and ultimately through the catheter. Moreover, a duct network 265 is shown connected to lower reservoir 250 and acts to direct fluid both from the lower reservoir port to lower reservoir 250 during a refill procedure and from lower reservoir 250 towards manifold 280, as will be discussed further below. As shown in FIG. 23, duct network 265 includes duct portions 265a and 265b, as well as other portions which will be discussed more fully below. FIG. 24 is another cross-sectional view of pump 210 taken along the line G-G of FIG. 21, which shows in more detail valve 275a. As shown, silicone valve cone 276a is provided in the valve assembly to ensure that no leakage of fluid passing around valve 275a occurs. Preferably, the silicone is roughed so as to ensure control of very small flow rates. However, many different surface treatments may be utilized. In one method of making such a roughened cone 276a, a mold is sand blasted in order to produce the roughened silicone components.

FIG. 24 also depicts other portions of duct assembly 265. Specifically, where FIG. 23 depicts duct portions 265a and 265b, FIG. 24 depicts duct portions 265c and 265d. Portion 265c includes a resistor capillary 265e, while portion 265d directs fluid expelled from lower reservoir 250 to valve 275b after having passed through capillary 265e.

Figure 25:
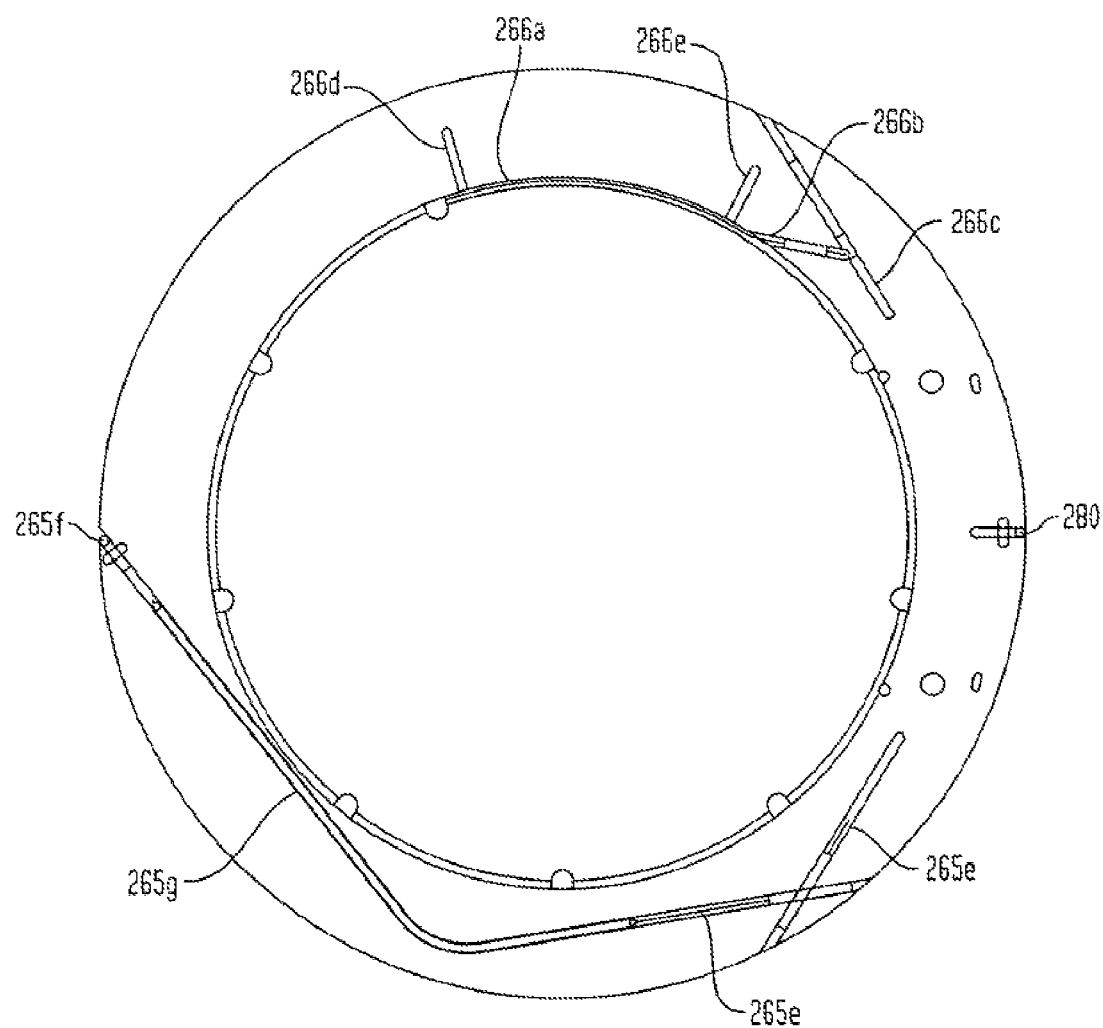
FIG. 25 is a top cross sectional view of an upper portion of the implantable pump shown in FIG. 16.

FIG. 25 further depicts duct network 265. Specifically, reference numeral 265f represents an opening where portion 265b and 265c meet. Portion 265d is shown to include a bend and a filter 265g within the duct. Essentially, duct 265c is a relatively large passage with a smaller filter 265f placed therein. The filter preferably prevents particulates or other matter within the fluid from being directed out of pump 210. FIG. 25 also illustrates where resistor capillary 265e is located. A center of manifold 280 can also be seen in the figure.

With regard to upper reservoir 252, a duct assembly 266 is provided and largely shown in FIG. 25. Duct assembly 266 includes a filter 266a which is situated along the interior perimeter of the portion shown in FIG. 25. Fluid dispelled from upper reservoir 252 can preferably enter duct assembly 266 along any portion of filter 266a. This fluid is ultimately directed to a resistor capillary 266b and thereafter to duct portion 266c which directs the fluid to valve 275a. In addition, duct assembly 266 includes a duct portion 266d which allows fluid from the upper reservoir refill port to enter upper reservoir 252 during a refill operation and a duct portion 266e which provides fluid from upper reservoir 252 to sensor 242a. Although not shown in FIG. 25, lower reservoir 250 is fluidly connection with sensor 242b.

Figure 26:
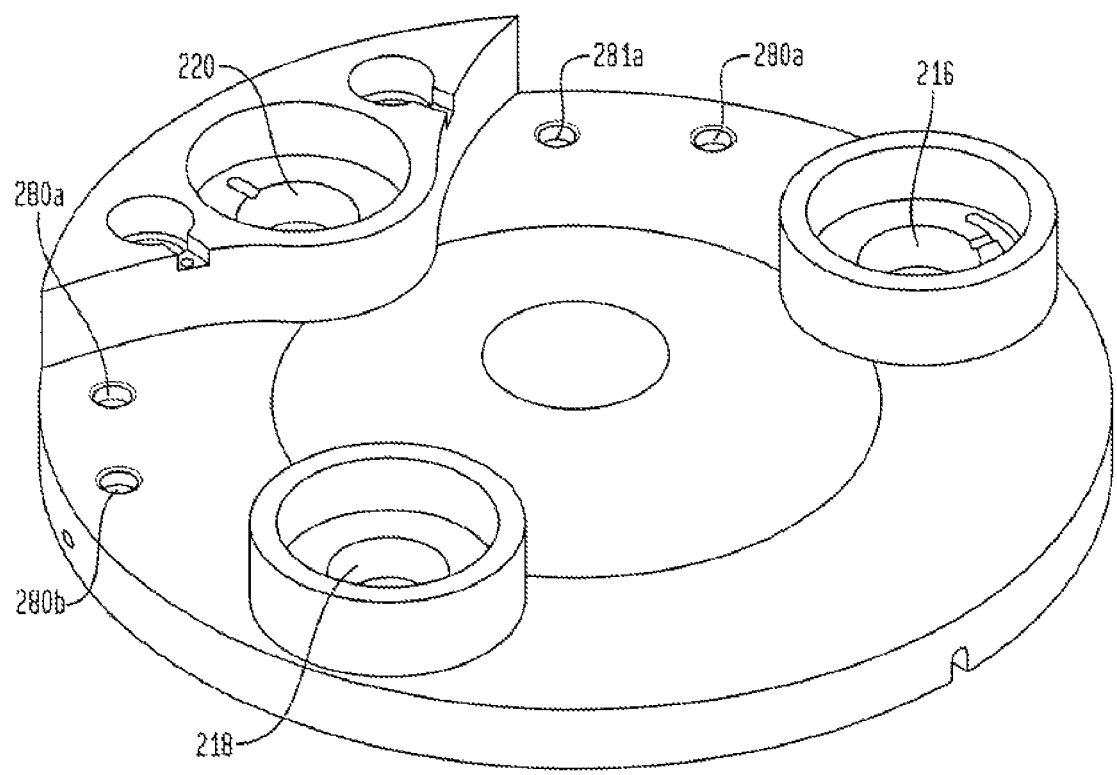
FIG. 26 is a top perspective view of the upper portion of the implantable pump shown in FIG. 16.
Figure 27:
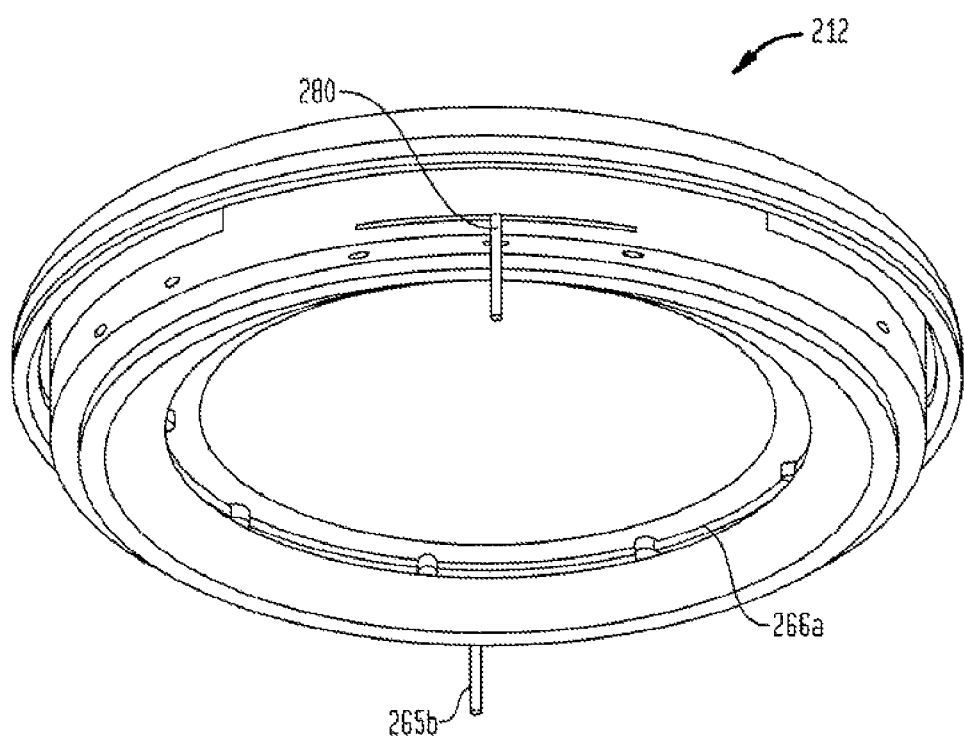
FIG. 27 is a lower perspective view of the upper portion shown in FIG. 26.

Upper portion 212 is shown in FIGS. 26 and 27 separated from all other components of pump 210. In FIG. 26, apertures 216, 218, and 220, can clearly be seen, as can sensor ports 280a and 282a for reception of the portion of sensors 242a and 244a extending below housing 228a and sensor ports 280b and 282b for reception of the portion of sensors 242b and 244b extending below housing 228b. Moreover, apertures 284a and 284b are shown and in which valves 275a and 275b ultimately reside. In FIG. 27, portion 265b can be seen, as can manifold 280 (also shown in FIG. 28). In addition, FIG. 27 depicts filter 266a and its connection to upper portion 212 via several glue spots or the like. In FIG. 28, manifold is shown separated from other portions of pump 210. As shown, the manifold operates to take three separate streams of fluid (i.e., fluid from the upper and lower reservoirs and from the catheter direct access port) and direct such to the catheter.

Operation of pump 210 is largely similar to that of pump 10, with the major differences residing in the structure to obtain that operation. The inclusion of separate hermetic housing in the design of pump 210 is beneficial from both a manufacturing and assembly standpoint. Moreover, the configuration of the valves and actuators of pump 210 allows for a hermetic sealing of only those components that are most susceptible to damage by the surrounding environment.

Figure 29:
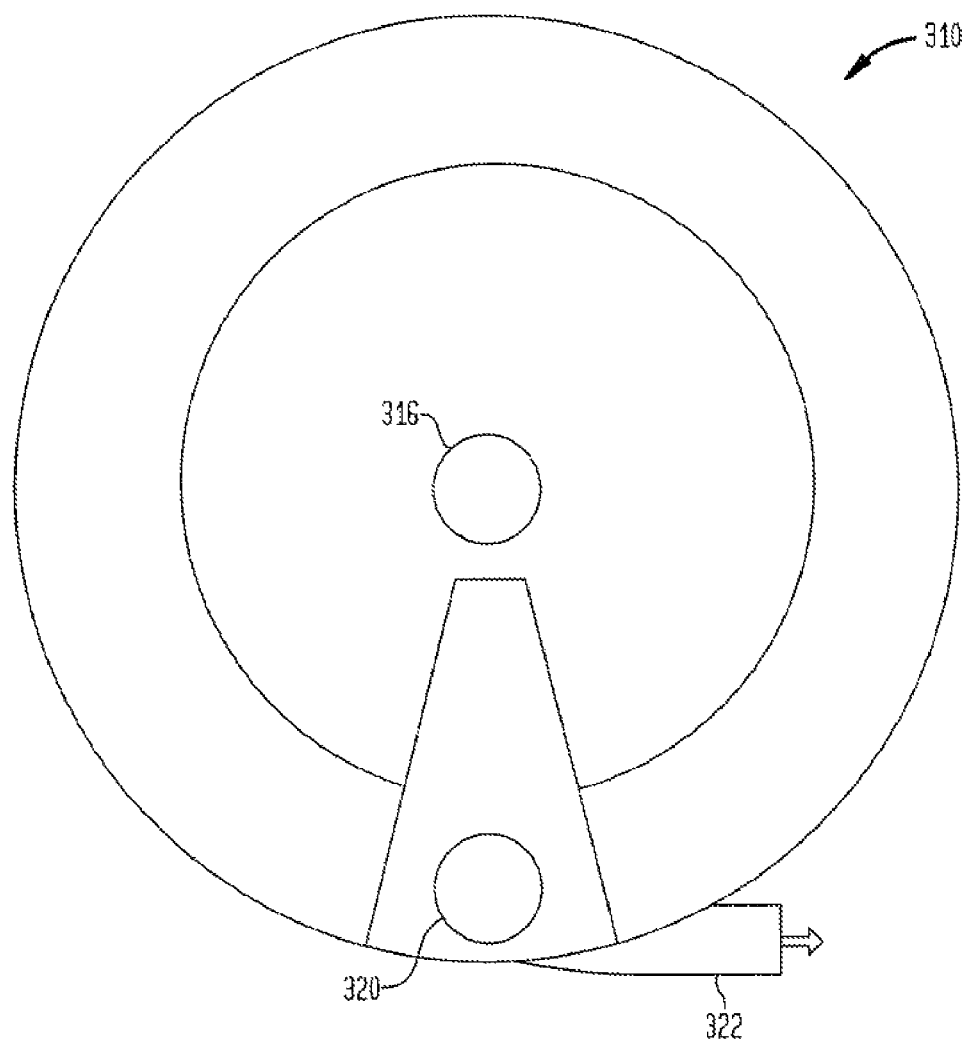
FIG. 29 is a top view of a multiple reservoir implantable pump in accordance with yet another embodiment of the present invention.
Figure 30:
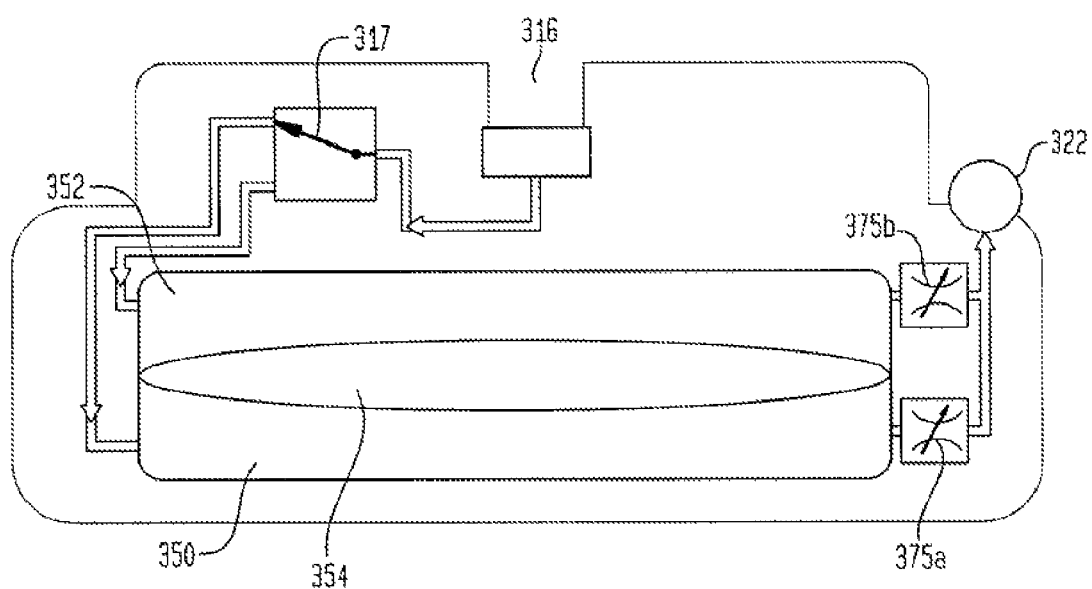
FIG. 30 is a schematic representation of the components included in the implantable pump shown in FIG. 29.

FIGS. 29 and 30 depict yet another embodiment pump 310. Like in pump 210, the different components of pump 310 will be referred to below with like reference numeral to that of pump 10, but within the 300-series of numbers. Pump 310 includes a central aperture 316 partially defining a refill port and a second aperture 320 partially defining a catheter direct access port. The refill port also includes a septum 332, while the catheter direct access port also includes a septum 334. The design of these septa may be like those known in the prior art, as is discussed above in connection with pumps 10 and 210.

The catheter direct access port, like in pumps 10 and 210, provides direct fluid access to a catheter connector 322. On the other hand, as is shown in FIG. 30, the refill port allows for fluid access to both a lower reservoir 350 and upper reservoir 352 (a propellant chamber 354 is shown therebetween like in the other embodiments). A programmable valve 317 is provided downstream of the refill port. This valve may be of any type known in the art or related arts and is preferably designed so as to be controllable by a medical professional or other operator during a refill procedure. For instance, valve 317 may be controlled wirelessly or via a mechanical trigger locate on the pump. Essentially, the orientation of valve 317 will dictate which reservoir is filled during a refill procedure.

The remainder of pump 310 may be similar to either of the above-discussed embodiments or even variations of each. For instance, FIG. 30 depicts two valves 375a and 375b, which may be designed in accordance with either the like valves of pump 10 or 210, or even in accordance with other known designs.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for dispensing first and second active substances at varying flow rates from a programmable pump system to a patient comprising:
   providing a pump housing defining an interior including a first chamber containing the first active substance, a second chamber containing the second active substance, and a third chamber containing a propellant;
   dispelling the first active substance from the first chamber at a first flow rate to a catheter fluidly connected to the first and second chambers;
   dispelling the second active substance from the second chamber at a second flow rate to the catheter;
   determining whether to actuate a first valve in fluid communication with the first chamber to vary the first flow rate based on a comparison of pressure readings taken by the first and second pressure sensors; and
   determining whether to actuate a second valve in fluid communication with the second chamber to vary the second flow rate based on a comparison of pressure readings taken by the third and fourth pressure sensors.

2. The method of claim 1, wherein the first and second active substances are identical.

3. The method of claim 1, wherein the third chamber is defined by first and second membranes.

4. The method of claim 3, wherein the housing includes first and second portions, the first and second membranes captured between the first and second portions so that the first portion and first membrane defines the first chamber and the second portion and second membrane defines the second chamber.

5. The method of claim 1, further comprising actuating the first valve using a first motor.

6. The method of claim 5, further comprising actuating the second valve using a second motor.

7. The method of claim 6, wherein the steps of actuating the first and second valves occur in planes parallel to a top plane of the housing and a bottom plane of the housing.

8. The method of claim 7, wherein the step of actuating the first valve is accomplished by the first motor rotating a first offset cam associated with the first motor and the first valve, and the step of actuating the second valve is accomplished by the second motor rotating a second offset cam associated with the second motor and the second valve.

9. The method of claim 6, wherein the steps of actuating the first and second valves occur in planes perpendicular to a top plane of the housing and a bottom plane of the housing.

10. The method of claim 9, wherein the step of actuating the first valve is accomplished by the first motor moving a first lever associated with the first motor and the first valve, and the step of actuating the second valve is accomplished by the second motor moving a second lever associated with the second motor and the second valve.

11. The method of claim 10, wherein the first and second pressure sensors and the first motor are contained within a first hermetic housing and the third and fourth pressure sensors and the second motor are contained within a second hermetic housing.

12. The method of claim 11, wherein the first hermetic housing includes a first aperture covered by a first membrane and the second hermetic housing includes a second aperture covered by a second membrane.

13. The method of claim 12, wherein the first membrane is associated with the first motor and the first lever and the second membrane is associated with the second motor and the second lever.

14. The method of claim 13, wherein a third hermetic housing is associated with the first and second hermetic housings.

15. The method of claim 14, wherein the third hermetic housing includes at least one power source and at least one electronic element.

16. The method of claim 1, further comprising filling the first chamber with the first active substance and filling the second chamber with the second active substance through a replenishment opening in the pump housing.

17. The method of claim 16, further comprising positioning a third valve in a first position whereby only the first chamber can be refilled, the third valve being in fluid communication with the replenishment opening and the first and second chambers.

18. The method of claim 17, further comprising positioning the third valve in a second position, whereby only the second chamber can be refilled.

19. The method of claim 18, further comprising actuating and actuation mechanism to position the third valve in either the first or second position.

* * * * *